United States Patent
Silk et al.

(10) Patent No.: US 9,226,503 B2
(45) Date of Patent: Jan. 5, 2016

(54) **COMPOSITION AND METHOD FOR ATTRACTION OF EMERALD ASH BORER *AGRILUS PLANIPENNIS* FAIRMAIRE (COLEOPTERA: BUPRESTIDAE)**

(71) Applicant: Her Majesty the Queen in Right of Canada, as represented by the Minister of Natural Resources Canada, Ottawa (CA)

(72) Inventors: Peter J. Silk, Frederiction (CA); David Magee, Gagetown (CA); Krista Ryall, Sault Ste. Marie (CA); Peter Mayo, Durham Bridge (CA)

(73) Assignee: Her Majesty the Queen, in Right of Canada, as represented by the Minister of Natural Resources Canada, Ottawa (CA)

( * ) Notice: Subject to any disclaimer, the term of this patent is extended or adjusted under 35 U.S.C. 154(b) by 0 days.

(21) Appl. No.: 14/518,221

(22) Filed: Oct. 20, 2014

(65) Prior Publication Data
US 2015/0132252 A1     May 14, 2015

Related U.S. Application Data

(63) Continuation of application No. 13/559,748, filed on Jul. 27, 2012, now abandoned.

(60) Provisional application No. 61/513,054, filed on Jul. 29, 2011.

(51) Int. Cl.
*A01N 43/22* (2006.01)
*A01N 31/02* (2006.01)

(52) U.S. Cl.
CPC ............... *A01N 43/22* (2013.01); *A01N 31/02* (2013.01)

(58) Field of Classification Search
None
See application file for complete search history.

(56) References Cited

PUBLICATIONS

Grant et al., J. Appl. Entomol., 134 (2010) 26-33.*
Bartelt et al., J. Chem. Ecol. (2007) 33:1299-1302.*
Francese et al., J. Econ. Entomol. 103(4): 1235-1241 (2010).*

* cited by examiner

*Primary Examiner* — Michael G Hartley
*Assistant Examiner* — Robert Cabral
(74) *Attorney, Agent, or Firm* — Catherine Lemay

(57) ABSTRACT

The invention disclosed relates to a novel composition and use thereof, for the attraction and detection of emerald ash borer, *Agrilus planipennis* Fairmaire. The composition comprises (3Z)-dodecen-12-olide and ash foliar or cortical volatiles (green leaf volatiles) associated with a prism trap of a color in the green range of the visible light spectrum. A significant increase in the capture of male *A. planipennis* is achieved when traps were deployed in the upper tree canopy. This invention is the first demonstration of increased attraction with a combination of a pheromone and a green leaf volatile in a Buprestid species.

7 Claims, 9 Drawing Sheets

Figure 1:
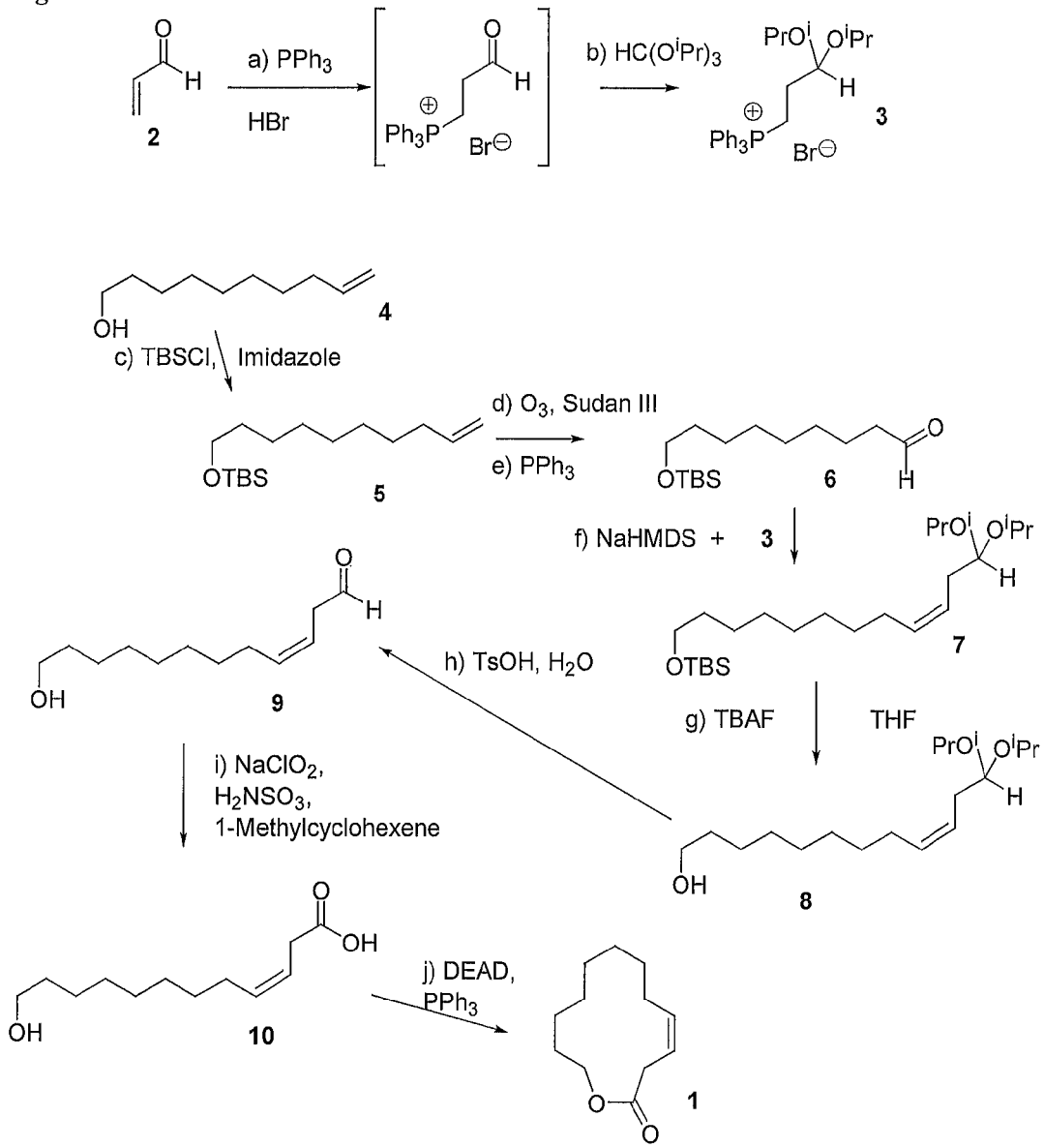

COMPOSITION AND METHOD FOR ATTRACTION OF EMERALD ASH BORER *AGRILUS PLANIPENNIS* FAIRMAIRE (COLEOPTERA: BUPRESTIDAE)

This application is a continuation of U.S. application Ser. No. 13/559,748 filed on Jul. 27, 2012 and claims the benefit of U.S. Provisional patent application 61/513,054 filed Jul. 29, 2011.

BACKGROUND OF THE INVENTION

The emerald ash borer, *Agrilus planipennis* Fairmaire, (Coleoptera: Buprestidae) is an invasive Palearctic species that has killed millions of ash trees (*Fraxinus* spp. L.) (Oleaceae) in the USA and Canada (Cappaert et al. 2005; Poland and McCullough 2006). Although initially detected near Detroit, Mich. in 2002, there is evidence that populations of this invasive species had been present in Michigan, USA and Ontario, Canada since the mid-1990s (Seigert et al. 2007). Since then, it has spread rapidly and has been detected in 15 states and two provinces, Ontario and Quebec, in Canada (EAB 2010). Movement of infested firewood and nursery stock has exacerbated its spread and large scale devastation of ash trees is predicted (Marchant 2006). Early detection of *A. planipennis* infestations has proven difficult because visual signs and symptoms, such as D-shape exit holes, epicormic shoots, bark deformities, and thinning crowns, usually appear only on heavily infested trees a year or more after populations have been established (Cappaert et al. 2005; de Groot et al. 2006, 2008; Poland and McCullough 2006). Development of a monitoring system is critical for early detection of *A. planipennis* populations, which would aid in management and control decisions. In order to maximize detection efficacy, a better understanding of the behavior and chemical ecology of adult *A. planipennis* is needed.

Adult *A. planipennis* are typically active between 0600-1700 h, particularly when the weather is warm and sunny (Yu 1992; Rodriguez-Saona et al. 2007), with mating occurring from 0900-1500 h and lasting for 20-90 min. Yu (1992) observed that adults preferred trees in open areas with direct sunlight and that during rainy or cloudy weather they tended to rest in cracks in the bark or on the foliage. Adult beetles, particularly males, spend much of their time in the canopy feeding and flying short distances (Lance et al. 2007; Lelito et al. 2007; Rodriguez-Saona et al. 2007). Indeed, traps in the mid-upper ash canopy capture more adults than traps hung below the canopy (Lance et al. 2007; Francese et al. 2007, 2008; Crook et al. 2008, 2009) and traps in locations exposed to direct sunlight (i.e. on the edge or near a gap) generally catch more adults than those in shaded locations (Poland et al. 2005; McCullough et al. 2006, 2009; Francese et al. 2008; Lyons et al. 2009).

Crook and Mastro (2010) reviewed the considerable progress made towards developing a trap that is effective at capturing *A. planipennis* (Francese et al. 2005, 2007, 2008, 2010; Crook et al. 2008, 2009; Lelito et al. 2007, 2008; McCullough et al. 2008). Color has been identified as an important factor affecting trap captures, with purple shown to be highly attractive (Francese et al. 2005, 2008; Crook et al. 2008). Purple traps typically catch more females than males (Francese et al. 2008; Crook et al. 2009), due to *A. planipennis* response to light in both the blue and red range of the visible spectrum (Crook et al. 2009). Currently, a sticky purple prism trap is utilized in surveys for *A. planipennis* in the United States (Francese et al. 2008; Crook and Mastro 2010). Adult *A. planipennis* also respond to green light in the 540-560 nm range of wave length 540-560 nm (Crook et al. 2009), with green traps capturing two to three times as many adults as purple traps. Crook et al. 2009 also found that dark green (24% reflectance) and light green (64% reflectance) caught more beetles than purple. Also, Francese et al (2010b) Can. Entomol. 142: 596-600 tested purple vs light green (540 nm, 64% reflectance) traps and reported that green caught more EAB, particularly males. Also, Francese et al. (2010a) J Econ Ent 103: 1235-1241 studied different green wavelengths and different reflectances, and concluded that the best trap would be a green trap with a wave length of 540 nm and 49% reflectance. Green traps typically have a bias towards males in trap captures (Lance et al. 2007; Rodriguez-Saona et al. 2007; Lelito et al. 2008; Crook et al. 2009). However, green traps typically catch more adults only when deployed high in the tree canopy. Thus, trap deployment, as well as color and lure combination, must be considered when evaluating traps for a monitoring program, as trap captures are likely influenced by adult preferences and behavioral activity patterns.

Numerous studies have described the chemical ecology of *A. planipennis* (Crook and Mastro 2010) and two types of host volatiles have been demonstrated to be attractive: bark sesquiterpenes (Poland and McCullough 2006; Crook et al. 2008) and green leaf volatiles (Poland et al. 2004, 2005, 2006, 2007; Rodriguez-Saona et al. 2006; de Groot et al. 2008; Grant et al. 2010). Girdled or stressed ash (Poland and McCullough 2006; Crook et al. 2008) are attractive to both sexes, as are Manuka and Phoebe oils which contain, in part, the sesquiterpenes emitted by stressed *Fraxinus* spp. (Crook et al. 2008; Crook and Mastro 2010; Grant et al. 2010). Of the green leaf volatiles, one compound in particular, (3Z)-hexenol, is highly antennally active and attractive to males (de Groot et al. 2008; Grant et al 2010). These results indicate that specific host volatiles act as kairomones in the chemical ecology of *A. planipennis* and these compounds may provide useful detection tools.

Much of the literature on the mating behavior of buprestids (e.g. Rodriguez-Saona et al. 2006; Lelito et al. 2007; Akers and Nielsen 1992; Gwynne and Rentz 1983; Carlson and Knight 1969) has described the use of visual and tactile cues for mate location. For buprestids, including those in the genus *Agrilus*, host location has been described as occurring first by olfactory processes and then mate location by visual, or by vibratory and/or tactile cues (Carlson and Knight 1969). However, Dunn and Potter (1988) showed attraction of *A. bilineatus* (Weber) males to cages containing females compared to host-logs only, suggesting the use of a female-produced pheromone.

Limited progress has been made into the pheromone chemistry of *A. planipennis*. Previous work suggested the presence of a contact pheromone (Lelito et al. 2007), subsequently identified by our research group as 9-methylpentacosane, which appears only on the cuticle of female *A. planipennis* at sexual maturity (7-10 d old) and stimulates full copulatory activity in males upon antennal contact (Silk et al. 2009), although 3-methyltricosane may also be involved as an additional component (Lelito et al. 2009). Bartelt et al. (2007) identified a volatile, antennally-active predominantly female-produced macrocyclic lactone, (3Z)-dodecen-12-olide [(3Z)-lactone], which was the first putative volatile pheromone described for *A. planipennis*, but no behavioral activity was reported.

Pureswaran and Poland (2009) reported that males were able to locate and identify females at close range using olfaction and an unidentified volatile cue. Here, we use GC-EAD in combination with field trapping and olfactometry to test whether (3Z)-lactone elicits behavioral responses in *A. planipennis* either alone or in combination with host kairomones (bark sesquiterpenes or green leaf volatiles). We tested various lure combinations on both purple and green traps, as both colors have been shown to be attractive. We also tested the lactone stereoisomer, (3E)-lactone, for its effect on *A. planipennis* behavior because preliminary studies suggested that exposure to UV-light catalyzes the isomerization of (3Z) to the (3E)-lactone and *A. planipennis* adults are known to favor sunny locations.

SUMMARY OF THE INVENTION

This invention provides the first behavioral evidence for a volatile pheromone of *A. planipennis* in combination with host foliar volatiles in association with a trap of a color in the green range of the visible light spectrum, contributing to the knowledge of the chemical ecology and the development of improved tools for the detection of *A. planipennis* infestations.

According to one aspect of the present invention, a composition for the attraction of *A. planipennis* is provided, comprising (a) (3Z)-dodecen-12-olide and (b) ash foliar volatiles, associated with a trap of a color in the green range of the visible light spectrum.

According to one embodiment of the composition aspect of the invention, the amount of (3Z)-dodecen-12-olide is a source dosage which emits 2.4-160 μg of (3Z)-dodecen-12-olide per day at about 25 0C.

According to another embodiment of the composition aspect of the invention, the ash foliar volatiles comprise (3Z)-hexenol.

According to yet another embodiment of the composition aspect of the invention, the ash foliar volatiles comprise (3Z)-hexenol of a source dosage which emits 50-100 mg per day at about 25 0C.

According to yet another embodiment of the composition aspect of the invention, the trap is a sticky prism tap of a green color defined by a wave length of 540-560 nm and a reflectance of 24-64% e.g. 540 nm and 49% reflectance.

According to yet another embodiment of the invention, the amount of (3Z)-dodecen-12-olide is a source dosage which emits 2.4-22 μg per day of (3Z)-dodecen-12-olide and the amount of (3Z)-hexenol is a source dosage which emits 40-60 mg per day of (3Z)-hexenol.

According to another aspect of the present invention, a method for the attraction of *A. planipennis* is provided, comprising applying to an insect habitat an insect attracting amount of (3Z)-dodecen-12-olide and ash foliar volatiles, associated with a trap of a color in the green range of the visible light spectrum.

According to one embodiment of the method aspect of the invention, the amount of (3Z)-dodecen-12-olide is a source dosage which emits 2.4-160 μg of (3Z)-dodecen-12-olide per day at about 25 0C.

According to another embodiment of the method aspect of the invention, the ash foliar volatiles comprise (3Z)-hexenol.

According to yet another embodiment of the method aspect of the invention, the ash foliar volatiles comprise (3Z)-hexenol of a source dosage which emits 50-100 mg per day at about 25 0C.

According to yet another embodiment of the method aspect of the invention, the trap is a sticky prism tap of a green color defined by a wave length of 540-560 nm and a reflectance of 24-64% e.g. wavelength 540 nm and 49% reflectance.

According to yet another aspect of the invention, a kit for the attraction of *A. planipennis* is provided, wherein the components (a) and (b) of the composition are maintained separately until use, and associated for use with a trap of a color in the green range of the visible light spectrum. The kit comprises a septum containing an insect attracting amount of (3Z)-dodecen-12-olide dissolved in a volatile solvent e.g. hexane which evaporates before use, leaving the (3Z)-dodecen-12-olide to emit therefrom, and a bubble cap containing an effective amount of neat ash volatiles e.g. (3Z)-hexenol, associated with the trap and maintained separately until use.

According to one embodiment of the kit aspect of the invention, the amount of (3Z)-dodecen-12-olide is a source dosage which emits 2.4-160 μg of (3Z)-dodecen-12-olide per day, and the ash foliar volatiles comprise (3Z)-hexenol of a source dosage which emits 50-100 mg per day, at about 25 0C, and wherein the trap is a prism sticky trap of a green color defined by a wave length of about 540-560 nm and a reflectance of 24-64%.

When a sticky trap is used, no insecticide is required. However, if a non-sticky trap is used, an appropriate insecticide is included.

BRIEF DESCRIPTION OF THE DRAWING

FIG. 1 is a flow diagram illustrating a process according to the invention for the synthesis of (3Z)-dodecen-12-olide.

FIG. 2 is a flow diagram illustrating a process according to the invention for the synthesis of (3E)-dodecen-12-olide.

FIG. 3 is a graph illustrating electroantennographic (EAG) dose-response curves of male and female *A. planipennis* antennae to (3Z)-dodece-12-olide (3ZLac) and (3E)-dodece-12-olide (3ELac) according to dosages applied to stimuli cartridges. EAG dose-responses (mean±SEM) are presented relative to a positive control standard (geranyl acetone, 1 μg applied dose).

FIG. 4 illustrates GC-FID/EAD responses of male and female *A. planipennis* antennae. The FID trace is a synthetic mixture of (3E)- and (3Z)-lactones.

FIGS. 5*a-d* are graphs illustrating proportions of male *A. planipennis* crawling up the test vs. control arms of a Y-tube olfactometer in 12 independent trials in response to: (a) (3E)-lactone, (3Z)-lactone or a 60:40 combination; (b) Phoebe oil (25 μl) alone or combined with either (3E)-lactone or (3Z)-lactone); (c) Phoebe oil (2.5 μl) alone or combined with (3E)-lactone or (3Z)-lactone; and (d) (3Z)-hexenol alone or combined with either (3E)-lactone or (3Z)-lactone. For each stimulus, the test treatment was compared with the control using a chi-square goodness of fit test.

FIGS. 6*a-c* are bar graphs illustrating mean (±SE) catches of male and female *A. planipennis* on purple sticky prism traps baited with various combinations of (3Z)- and/or (3E)-lactone and host volatiles in field experiments carried out at two sites in (FIG. 6*a*) 2008 and two sites (FIG. 6*b-c*) in 2009. Sites were analyzed separately in 2009 due to the differences in sex ratio. Note differences in scale of X-axis. Prior to analyses, data were transformed using a natural log (n+1), however untransformed data are presented. Error bars reflect + or − one standard error of the least squares means. In 2008 (FIG. 2*a*), (3E)-lactone was not tested except that it was present in the synthetic (3Z)-lactone at 2%.

FIGS. 7*a-b* are bar graphs illustrating mean (±SE) catches of male and female *A. planipennis* on green sticky prism traps baited with the different attractant combinations at (FIG. 7*a*) Anika and McKellar sites combined and (FIG. 7*b*) sites in Michigan, USA. Plotted values reflect the least squares means of 12 replicate blocks in total (untransformed data). Statistics (P>F) apply to natural log (n+1)-transformed data following ANOVA. Error bars reflect + or − one standard error of the least squares means.

Figure 8:
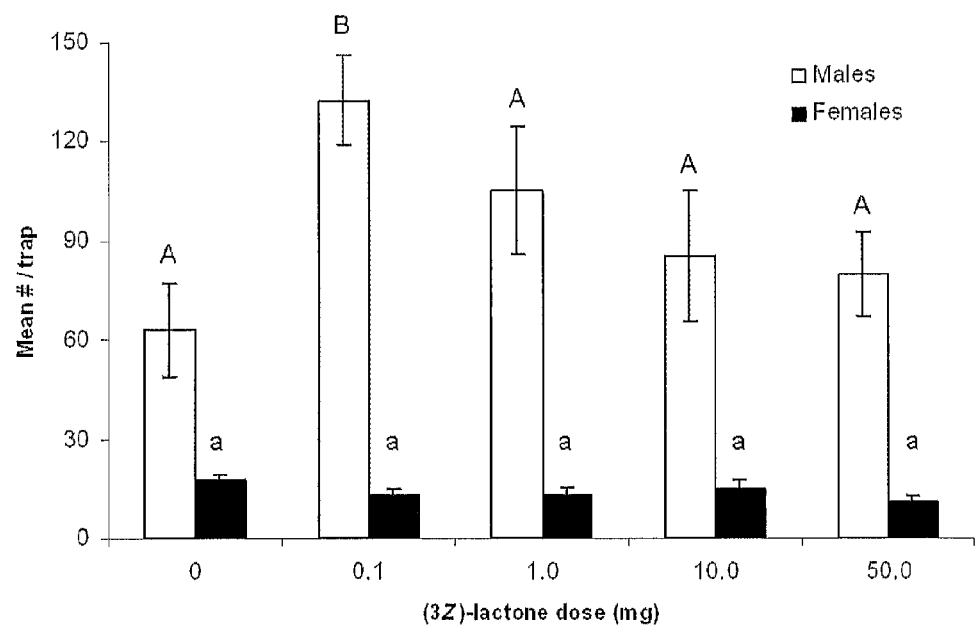

FIG. 8. Dose-response curve for male and female *A. planipennis* to increasing dose of (3Z)-lactone loaded on rubber septa and deployed on dark green sticky traps in combination with (3Z)-hexenol. Plotted values reflect the means of 10 replicate blocks in total (untransformed data). Statistics (p>F) apply to natural log (n+1)-transformed data following ANOVA. Error bars reflect + or − one standard error of the mean. Letters above bars indicate significant differences among treatments compared against the control within each sex.

Figure 9:
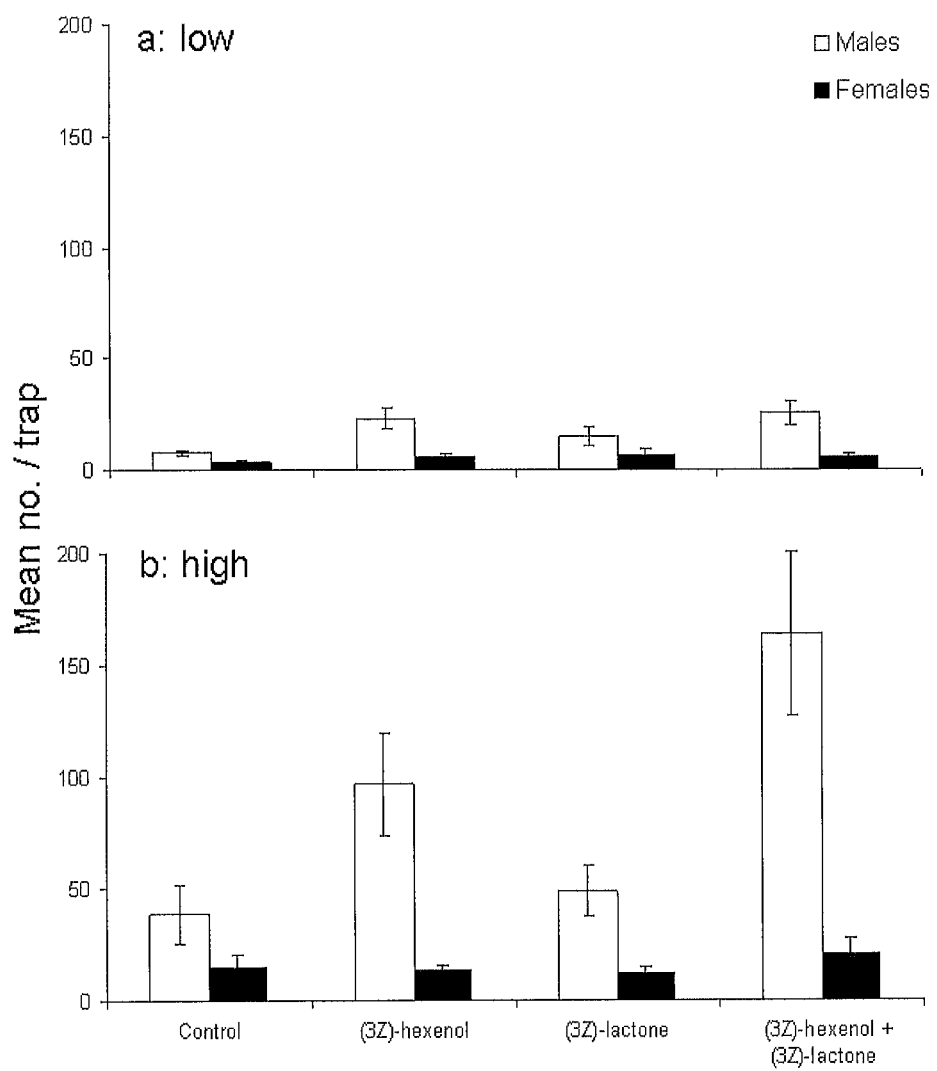

FIG. 9 (a and b). Influence of (3Z)-lactone with and without (3Z)-hexenol on attraction of male and female *A. planipennis* to dark green sticky traps placed at different heights with respect to the ash canopy: (a) low and (b) high. Plotted values reflect the least squares means of 10 replicate blocks in total (untransformed data). Statistics (p>F) apply to natural log (n+1)-transformed data following ANOVA. Error bars reflect + or − one standard error of the least squares means.

DETAILED DESCRIPTION OF THE INVENTION

Methods and Materials

Source of Insects.

Trees with larval *A. planipennis* were felled near Windsor and Sarnia, Ontario; infested logs were transported to the Great Lakes Forestry Centre in Sault Ste Marie, Ontario. Storage and rearing protocols have been previously reported (Silk et al. 2009). Emerged adults were sexed and virgin males and females were kept on a 16:8 h L:D cycle and supplied with water and foliage of evergreen ash, *Fraxinus uhdei* (Wenzig) Linglesh.

Volatile Collection.

Volatiles were collected from two groups of virgin adult males (n=18 and n=8) and two groups of virgin adult females (n=17 and n=18) feeding on ash leaves in separate 250 ml glass chambers (16:8 L:D at 22° C.). Adults were 10 d old when placed in the chambers in groups of 6-8 at one time; and were replaced as they died over the volatile collection period. Filtered air was drawn from the chambers at ~0.1 L/min onto a pre-conditioned Super-Q® filter (~200 mg) for 10-11 d. Volatiles were eluted using methylene chloride (3×2 mL) and concentrated to 10-20 µl under dry nitrogen.

Analytical Techniques and Purification.

Synthetic samples and extracts were analyzed by GC/MS on a Hewlett-Packard 5890 GC and a 5971 mass selective detector in the electron impact (EI, 70 eV) mode (Silk et al. 2007). The column used for analysis was a Supelco SPB-5 capillary (30 m×0.32 mm×0.25 µm film) in the splitless mode with helium as carrier gas. The injection port was at 220° C. and the oven temperature was programmed from 70° C., held for 1 min and then increased at 10° C./min to 240° C. and held for 30 min. Compounds were purified by flash chromatography on silica gel and, when required, by Kugelrohr distillation.

NMR ($^1$H and $^{13}$C) was carried out on a Varian Innova 300 MHz spectrometer in CDCl$_3$ with TMS as internal standard. IR spectra were recorded as thin liquid films on KBr discs with a Perkin Elmer 727B IR-spectrometer.

Chemical Synthesis.

The macrocyclic lactone, (3Z)-dodecen-12-olide (1) (FIG. 1), was synthesized according to the procedure described by Boden et al. (1993) and used by Bartelt et al. (2007) with the addition of a tert-butyldimethylsilyl (TBS) protecting group (which doubled the yield of the Wittig step). This involved ozonolysis of a TBS-protected alkenol (5) into a protected hydroxyaldehyde (6), Wittig reaction with a Wittig salt containing a protected aldehyde (3), removal of the TBS group to give 8, then hydrolysis of the acetal to give a (3Z)-unsaturated aldehyde 9, Lindgren oxidation (Lindgren and Nilsson 1973) to a carboxylic acid (10) and finally a Mitsunobu esterification (Kurihara et al. 1976) to effect the macrolactonisation. The synthesis of (3Z)-dodecen-12-olide was, therefore, successfully accomplished with the IR spectra, EI (70 eV) mass spectra and $^1$H and $^{13}$C NMR spectra closely matching those reported (Boden et al. 1993). Formation of (2E)-dodecen-12-olide and (3E)-dodecen-12-olide were found to be intrinsic to the synthesis at approximately 3% each. The (2E)-product, characterized by $^1$H NMR, was readily separated from the desired (3Z)-lactone by column chromatography. The (3E)-lactone, however, could not be separated from the (3Z)-lactone. $^1$H NMR supported the presence of ca. 3% of (3E)-lactone in the product.

Figure 2:
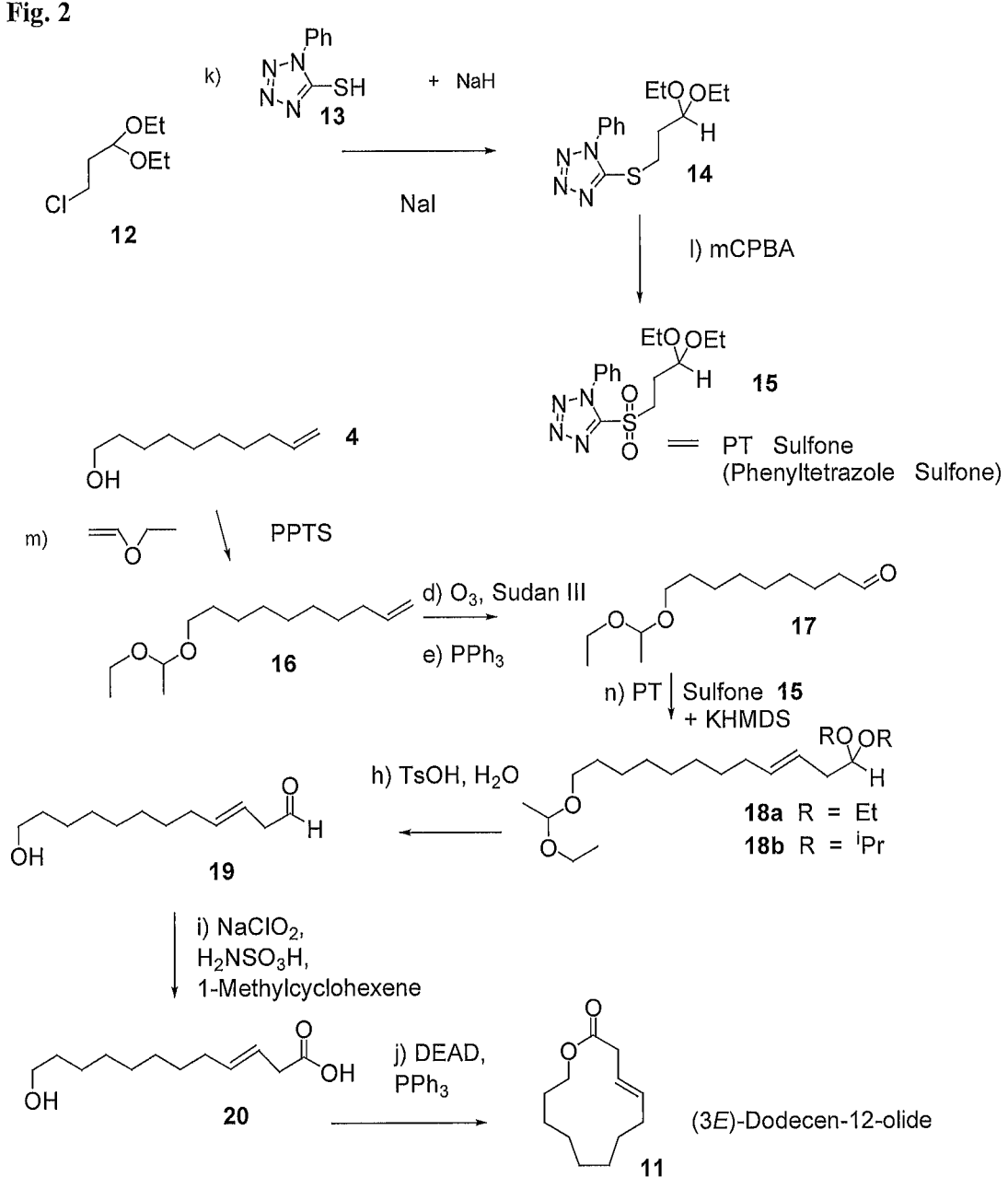

The 3E-lactone [(3E)-dodecen-12-olide] (11) (FIG. 2) synthesis was successfully accomplished by a Julia-Kocienski olefination according to the methodology described by Blakemore et al. (1998). The Julia-Kocienski olefination of aldehyde 17 proceeded with 34% yield and ca 97% E stereochemistry (FIG. 2) to give olefin 18a. Thus, protection of alkenol 4 with ethyl vinyl ether (EVE) proceeded smoothly to give 16, and ozonolysis with reductive workup gave aldehyde 17. The phenyltetrazole (PT) sulfone 15 was synthesized by deprotonating 1-phenyl-1H-tetrazole-5-thiol 13 with sodium hydride and coupling it with commercially available 12 to give thioether 14. mCPBA oxidation of 14 furnished the PT sulfone 15. After the Julia-Kocienski olefination, double hydrolysis of the two acetals of 18a gave 19 and Lindgren oxidation of 19 gave the hydroxyacid 20. Finally, as reported by Boden et al. (1993), activation of the hydroxyl group using the Mitsunobu method modified according to Steglich (Justus and Steglich 1991) gave (3E)-dodecen-12-olide 11 in an overall yield of 14% from alkenol 4. Spectral data for (3E)-lactone [(3E)-dodecen-12-olide)] 11:

$^1$H NMR (CDCl$_3$, 400 MHz): δ 5.47-5.62 (10 line symmetrical multiplet, 2H), 4.12 (AA'XX', 2H), 2.98 (d, 2H, J=7.0 Hz), 2.05 (m, 2H), 1.57 (m, 2H), 1.29-1.42 (m, 10H); $^{13}$C NMR (CDCl$_3$, 100 MHz): δ 172.0, 135.4, 123.2, 64.5, 39.0, 31.4, 27.2, 26.34, 26.28, 25.7, 24.9, 23.6. IR (neat): cm$^{-1}$ 3027 (w), 2928 (s), 2855 (s), 1733 (s), 1666 (w), 1457 (w), 1375 (w), 1348 (w), 1246 (s), 1143 (m), 1111 (m), 1039 (m); MS (EI) Major peaks: 41 (base peak), 54, 67, 81, 95, 109, 121, 136, 150, 168, 178, 196.

Schlosser modification of the Wittig reaction (Schlosser and Christmann 1966) was initially employed in an attempt to make 18b starting from Wittig salt 3 and aldehyde 17, however, the E-selectivity of the reaction was very capricious, with 80% stereochemical purity being the best result out of a dozen attempts at the reaction. This was deemed to be unacceptable, and the much better ~97% stereochemical purity obtained with the Julia-Kocienski olefination which gave 18a was much more satisfactory. Reagents and conditions of the syntheses of (3Z)-lactone and (3E)-lactone are as follows.

FIG. 1 Synthesis of (3Z)-Dodecen-12-olide 1 ((3Z)-lactone) (after Boden et al. 1993).

a) 2-Propanol, HBr, CH$_2$Cl$_2$. PPh$_3$, −10° C.-RT b) HC(O$^i$Pr)$_3$, one pot c) TBSCl, imidazole, DMF, RT d) O$_3$. Sudan III, CH$_2$Cl$_2$, −78° C. e) PPh$_3$, −78° C.-RT f) 3+NaHMDS, PhCH$_3$/THF (4:1), 0° C.-RT, then 6, −99° C.-RT g) TBAF, THF, RT h) TsOH, wet THF, reflux i) NaClO$_2$, H$_2$NSO$_3$H, 1-methylcyclohexene, CH$_2$Cl$_2$/H$_2$O (1:3), 0° C.-RT j) DEAD, PPh$_3$, PhCH$_3$, RT. HBr=Hydrobromic acid, CHCl$_2$=Dichloromethane, PPh$_3$=Triphenylphosphine, HC(OPr)$_3$=Triisopropylorthoformate, TBSCl=tert-butyldimethylsilyl chloride, DMF=Dimethylformamide, O$_3$=Ozone, NaHMDS=Sodium Hexamethyldisilylamide, PhC$_3$H=Toluene, THF=Tetrahydrofuran, TBAF=tetrabutylammonium fluoride, TsOH=para-Tolunesulfonic acid, NaClO$_2$=Sodium chlorite, H$_2$NSO$_3$H=Sulfamic acid, DEAD=Diethyl azodicarboxylate FIG. 2 Synthesis of (3E)-Dodecen-12-olide 11 ((3E)-lactone); modified Julia-Kocienski olefination. k) 13+NaH, DMF, 0° C.-60° C., then 12, NaI, 60° C. l) mCPBA, NaHCO$_3$, CH$_2$Cl$_2$, RT m) EVE, PPTS, CH$_2$Cl$_2$, RT n) 15+KHMDS, DME, −55° C., then 17, −55° C.-RT. NaH=Sodium hydride, NaI=Sodium iodide, mCPBA=meta-Chloroperoxybenzoic acid, NaHCO$_3$=Sodium bicarbonate, EVE=Ethyl vinyl ether, PPTS=Pyridinium para-toluenesulfonate, KHMDS=Potassium hexamethyldisilylamide, DME=1,2-Dimethoxyethane.

GC-EAD Analysis and EAG Dose-Response Study.

EAG analyses were made by methods and equipment generally described by Cossé & and Bartelt (2000). EAG connections were made by inserting a glass-pipette silver-grounding electrode into the back of an excised beetle head. A second glass-pipette silver-recording probe was placed in contact with the distal end of one antenna. Both pipettes were filled with Beadle-Ephrussi (Ephrussi and Beadle 1936) saline.

For the EAG-dose-response study, (3Z)- and (3E)-lactones were purified (99.9% purity by GC/MS) by high performance liquid chromatography (HPLC) using a Waters 515 pump, a Waters R401 refractive index detector, and a 25 cm by 0.46 cm i.d. silica column (Adsorbosphere Silica 5 µm, Alltech, Deerfield, Ill.), treated with silver nitrate as described by Heath and Sonnett (1980). Solvent was 8% ether in hexane. Ten micro liters of serially diluted solutions (methylene chloride) of synthetic (3Z)-lactone and (3E)-lactone were applied to filter paper strips (0.5 cm×5 cm, Whatman no. 1). The filter paper strips were placed in 14-cm-long Pasteur pipettes, hereafter referred to as stimulus cartridges, after 5 min at room temperature. Stimulus doses tested were 0.01, 0.1, 1, 10, and 100 µg. Male and female antennae were exposed to single 0.2s puffs of odor-bearing air at 5 ml/s by placing the tip of an stimulus cartridge into a hole of a glass tube (0.7 cm ID×20 cm), 10 cm from the outlet and 11 cm away from the antennal preparation. Airflow through the glass tube was humidified and set at 10 ml/s. Puff duration and airflow speeds were maintained by a stimulus flow controller (SFC-2, Syntech, Hilversum, The Netherlands). Stimuli cartridges were selected in random order, beginning with the lowest dosages and working upward to the highest dosages. Each puffed dosage was preceded and followed by a puff from a solvent blank cartridge (filter paper plus solvent). To compensate for possible deterioration of the antennal preparation, a standard control compound, geranyl acetone (1 µg dose) preceded dosages of stimuli compound. EAG amplitudes were normalized according to the responses to geranyl acetone by dividing the amplitude of the EAG generated by the test compounds by that of geranyl acetone. Dose-response series were replicated, using different antennal preparation for each replication, and the EAG responses were expressed as a percentage of the EAG responses to geranyl acetone. Each antennal preparation was tested with freshly prepared sets of stimuli cartridges. Male and female EAG responses were submitted to analysis of variance (ANOVA) using Statistica for Windows software (StatSoft Inc. Tulsa, Okla.)).

A Varian CP-3380 gas chromatograph with FID detector was modified for use with a GC-EAD signal recording device (IDAC-232). EAG data were analyzed using Syntech GC-EAD software v.2.6 (SYNTECH, The Netherlands). The column used for analysis was a Supelco SPB-5 capillary (30 m×0.32 mm×0.25 µm film) in the splitless mode with helium as carrier gas. The injection port was at 220° C. and the oven temperature was programmed from 70° C., held for 1 min and then increased at 10° C./min to 240° C. and held for 30 min. A number of GC-EAD runs on male and female volatiles were carried out. Both the (3Z)-lactone and (3E)-lactone were diluted to 10 µg/ml in hexane; 1 µl of diluted pheromone was injected for each GC-EAD run.

Ten nanograms was injected for the GC-EAD analysis consisting of 90% (3Z)-lactone and 10% (3E)-lactone using a DB-1 (15 m×0.25 mm ID, 1 µm film) capillary column (J&W Scientific, Folsom, Calif.). The GC oven temperature program was 50° C. for 1 min, then increased at 20° C./min and held at 280° C. for 2 min. The GC-EAD responses of five male and five female EAB antennae were analyzed.

Effect of Light on (3Z)-Lactone.

To determine whether light would promote the isomerization from (3Z) to (3E)-lactone, 20 mg of (3Z)-lactone was placed neat on a glass slide 10 mm below a UV light (UVG-54 handheld UV-lamp, 254 nm, 6w; UVP Upland Calif., USA) for three d. Subsamples (taken as ~1 mg in a pipette) were analyzed by GC/MS at regular intervals and the ratio of (3E):(3Z)-lactone was recorded. In addition, 6 mg of each of (3Z)- and (3E)-lactones (neat) were coated on the quartz surface of a cuvette and exposed outdoors to sunlight at 11° C. mean temperature for 9 d for an average of 5 h a day. Finally, (3Z)-lactone was coated (4 mg) on the dorsal surface of abdomen and elytra of 3 female EAB cadavers that were exposed to sunlight for 6 h per day for 1, 2 or 3 d at 10° C. mean temperature; cadavers were stored at 4° C. between sunny days. The lactones were removed from cuvettes and cadavers with hexane washing and analysed by GC/MS to determine the E:Z ratio.

Two-Choice Olfactometer Assays.

A Y-tube olfactometer (Analytical Research Systems Inc, Gainsville, Fla.) was used to test for attraction of *A. planipennis* to lactone isomers and host volatiles. The glass olfactometer (1.5 cm i.d.) had an 11 cm main stem that branched into two 9-cm arms. Each arm was connected to a cylinder that contained the stimulus. Charcoal filtered air was passed into each arm at a flow rate of 1.2 L/min. Treatments included the pheromone alone: (3Z)-lactone (10 µg); (3E)-lactone (10 µg); and 60:40 (3E):(3Z)-lactone (10 µg). Next, we tested bark sesquiterpenes and a green leaf volatile alone: Phoebe oil (25 µg and 2.5 µg) and (3Z)-hexenol (5 µg). We then tested the pheromone combined with bark sesquiterpenes: (3Z)-lactone (10 µg)+Phoebe oil (at both 25 µg and 2.5 µg); (3E)-lactone (10 µg)+Phoebe oil (at both 25 µg and 2.5 µg). Finally, we tested the pheromone combined with the green leaf volatile: (3Z)-lactone (10 µg)+(3Z)-hexenol (5 µg); and (3E)-lactone (10 µg)+(3Z)-hexenol (5 µg). Each stimulus (1 µl for single compound treatments and a total of 2 µl for two-compound treatments) was diluted in hexane, placed on a strip of filter paper and given one minute for the solvent to evaporate before being placed in the olfactometer. A second filter paper, treated with the equivalent volume of solvent was placed in the other arm of the olfactometer to serve as the control. The apparatus was rinsed with acetone after each treatment, and the arm attached to the test stimulus was randomized between replicates.

For each treatment, we tested increasing numbers of adults until we obtained a minimum of 12 beetles responding to the stimuli (either positively or negatively). To obtain this minimum, we tested 15-54 beetles per treatment. For each trial, a single *A. planipennis* (mature virgin male or female, >10 days old) was given ten minutes to choose between the two stimuli; adults were used only once in the bioassay. A choice was recorded when the beetle passed a "finish line", 7 cm beyond the branching point of each arm. 'No choice' was recorded if the beetle failed to pass either finish line after the ten minutes. Beetles that did not select either the stimulus or the control (i.e., no choice) were excluded from a subsequent chi-square goodness of fit test used to test whether the ratio of beetles choosing the stimulus vs. the hexane control differed significantly from 1:1. A chi-square test was conducted for each independent trial.

Field trapping. Three trapping experiments were carried out in green ash plantations (*F. pennsylvanica* Marsch) with low-to-moderate *A. planipennis* populations about 40 km southeast of Sarnia, Ontario (42° 58' 0 N, 82° 24' 0 W) in 2008, 2009 and 2010. Trees at these sites were generally healthy in appearance with low or no signs of decline, and only a small number of trees had obvious signs/symptoms of infestation by *A. planipennis*. In Ontario sites, trees were 20-25 years old, 4-6 m tall, 10-15 cm in diameter, and spaced about 2 m apart within a row and 2.5 m between rows. In 2010, the trapping experiment was replicated at four sites in Michigan, USA, in addition to the sites in Ontario. Sites in Michigan were 10-100 years old, 10-30 m tall, 15-70 cm in diameter, and located in a mixed woodlot. Corrugated plastic "prism" traps (0.30 cm×35.00 cm×58.75 cm) were coated with stickem (Crook et al. 2008) (Synergy Semiochemicals Corp., Burnaby, BC) and hung using rig spreaders (Zing Products, Westport Mass., USA). Purple traps were suspended from metal stands at a height of 1.5 m (2008-2009), whereas green traps were hung in the mid-canopy from ropes tied between two trees at 2.5 m in Ontario and at 6 m height in Michigan (2010). In Michigan, traps were hung from a single line thrown over the lowest canopy branch. Light green traps (approx 540 nm wavelength) were the same as used by Francese et al. (2010). Traps were set within 1.5-2 m of trees, spaced 20-30 m apart, in a randomized complete block design. Traps were checked every 2 weeks and *A. planipennis* were collected, counted and sexed.

Experiment 1, conducted in Ontario in 2008, was designed to test for attractiveness of (3Z)-lactone (Bartelt et al. 2007), alone and in combination with two types of host volatiles: bark sesquiterpenes (Crook et al. 2008) and a binary blend of green leaf volatiles ((3Z)-hexenol and (2E)-hexenol) (Poland et al. 2005, de Groot et al. 2008). We used purple prism traps, which at the time of this experiment were shown to be more attractive than traps of other colors (Francese et al. 2005), and which had been used successfully in other recent trapping experiments for *A. planipennis* (Crook et al. 2008, de Groot et al. 2008). Traps were baited with one of the following treatments: (3Z)-lactone; Phoebe oil (Synergy Semiochemicals Corp., Burnaby, BC); (3Z)-lactone+Phoebe oil; green leaf volatiles (GLVs) consisting of two bubblecaps, one containing (3Z)-hexenol and the other containing (2E)-hexenol (ConTech, BC); (3Z)-Lactone+GLVs; and unbaited controls. We selected Phoebe oil because it contained two additional sesquiterpenes that had been detected in ash trees and appeared to be more attractive than Manuka oil (Crook et al. 2008) and the (3Z)-hexenol and (2E)-hexenol combination based on results from de Groot et al. (2008). Release rates at 20° C. were estimated by weight loss as ca. 50 mg/d, 17 mg/d and 16 mg/d for Phoebe oil, (3Z)-hexenol, and (2E)-hexenol, respectively. (3Z)-lactone was emitted at ca. 80 μg/d at 20° C. from red rubber septa (Wheaton) impregnated with 5.0 mg per lure. Traps were out 10-24 Jun. 2008, replicated with 3 blocks at one site (Site A: Conservation area) and 7 blocks at the second site (Site B: Union Gas site). Lures were not changed during the experiment.

Experiment 2, conducted in Ontario in 2009, was designed to test the attractiveness of (3E)- vs. (3Z)-lactone, alone and in combination with Phoebe oil, based on results from 2008. Purple prism traps were baited with the following lure treatments: (3Z)-lactone; (3E)-lactone; Phoebe oil; (3Z)-lactone+Phoebe oil; (3E)-lactone+Phoebe oil; and unbaited controls. As in 2008, release rate of phoebe oil was ca. 50 mg/d at 20° C. The lactone lure consisted of a 1.5 ml PCR tube containing 50 mg of either (3E)- or (3Z)-lactone; a pipe cleaner wick was placed into the vial through a 1.0 mm hole with 2.0 mm of the wick protruding through the top of the tube (release rate=~0.5 mg/d at 20° C. Traps were in the field from 2 Jun.-4 Aug. 2009, with 7 blocks at one site (Site B: Union Gas site) and 8 blocks at the other (Site C: Anika Mills site). Lures were not changed during the experiment.

Experiment 3, conducted in 2010, was designed to test the effect of the single green leaf volatile, (3Z)-hexenol (de Groot et al. 2008, Grant et al. 2010), as a potential kairomone in combination with either (3Z)- or (3E)-lactone. We used green sticky prism traps deployed in the ash canopy, which had recently been demonstrated to capture more *A. planipennis* than purple traps (Francese et al. 2008; Crook et al. 2009) particularly when baited with (3Z)-hexenol (Grant et al. 2010). Treatments tested were: (3Z)-lactone; (3E)-lactone; (3Z)-hexenol; (3Z)-lactone+(3Z)-hexenol; (3E)-lactone+(3Z)-hexenol; and unbaited controls. (3Z)- and (3E)-lactone were loaded at a source dosage of 1.0 mg each and emitted ~22 ng/d at 25° C. from red rubber septa (Wheaton). The source dosage of 1.0 mg is taken from a solution of the lactone in hexane, which is absorbed into the red rubber septum. The solvent evaporates from the septum, which then emits the lactone at an effective rate of ~22 μg/d at 25° C. This experiment was replicated in Ontario and the Michigan. In Ontario, traps were out 1 Jun.-14 Jul. 2010 with 7 blocks at one site (Anika Mills site) and 5 blocks at another site (McKellar conservation area). Traps were hung at 2.5 m above the ground in the bottom edge of the canopy. In Michigan, traps were out from 25 May-7 July at four different sites. All traps in Michigan in 2010 were deployed below the canopy; the trees were 10-30 m in height. The lactone lures were replaced every two weeks; the other lures were unchanged.

The effect of each attractant on mean catch of female and male *A. planipennis* was analyzed independently using ANOVA and a randomized complete block design. Sites were analyzed separately in 2009 due to differences in sex ratios. In 2010, sites in Ontario were analyzed separately from those in Michigan due to the considerable differences in stand conditions and height of traps with respect to the ash canopy. In all three experiments, a priori hypotheses about the treatments were tested with contrasts; tests were conducted as one-sided tests for increases in trap captures. The first contrasts tested whether a single-component lure ((3E)- or (3Z)-lactone, Phoebe oil or GLV) caught more beetles than the unbaited control; a second set of contrasts compared captures of two-component lures vs. single component lures to test for the effect of adding the second component. Residuals were tested for homogeneity of variance and normality, and a $\ln(y+1)$ transformation was used where necessary. We present the untransformed least squares treatment means and their standard errors, along with statistics (P>F) from ANOVA of transformed data. For the two component traps, the foliar volatiles, in this case comprising (3Z)-hexenol, is provided in a separate emitter ie. a 'bubble cap" emitter from Contech of Vancouver, Canada, associated with the trap and containing a source concentration of 2-3 g of neat material, which emits 40-60 mg per day.

Results

GC/MS of Collected Volatiles.

GC/MS analysis of extracts from female volatiles confirmed the presence of the (3Z)-lactone with retention time and EI-mass spectra identical with the synthetic material. The (3E)-lactone, if present, was below the detection limit (ca. <200 picograms injected) and could not be confirmed as being emitted by females in the laboratory. Neither lactone was detected in volatiles collected from male *A. planipennis*.

EAG Dose-Response Study and GC-EAD Analysis.

Figure 3:
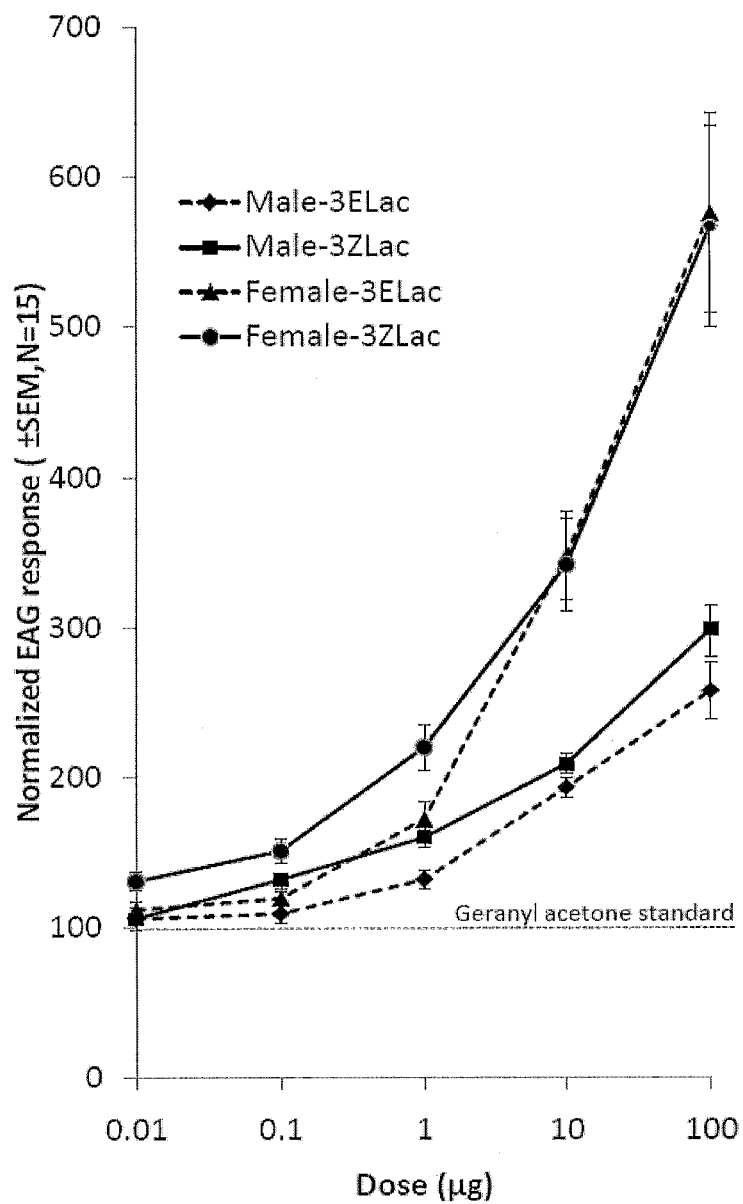

The EAG dose-response curves of male and female *A. planipennis* antennae for the two isomers of synthetic lactone are presented in FIG. 3. Female antennae did not respond differently to the (3Z)- and (3E)-lactone ($F_{1,149}=0.01$, $P=0.91$). Similar results were obtained with the male antennae ($F_{1,149}=2.3$, $P=0.14$). However, female antennae were more responsive to both (3Z)-lactone ($F_{1,149}=45.3$, $P<0.0001$) and (3E)-lactone ($F_{1,149}=39.8$, $P<0.0001$) than male antennae, particularly at higher doses. The mean responses of *A. planipennis* antennae to the geranyl acetone standard (1 µg applied dose) was $-0.06\pm0.03$ mV ($\pm$SD, n=80, 15 antennal preparations), while those to the solvent/air controls measured $-0.03\pm0.03$ mV ($\pm$SD, n=45, 15 antennal preparations).

Figure 4:
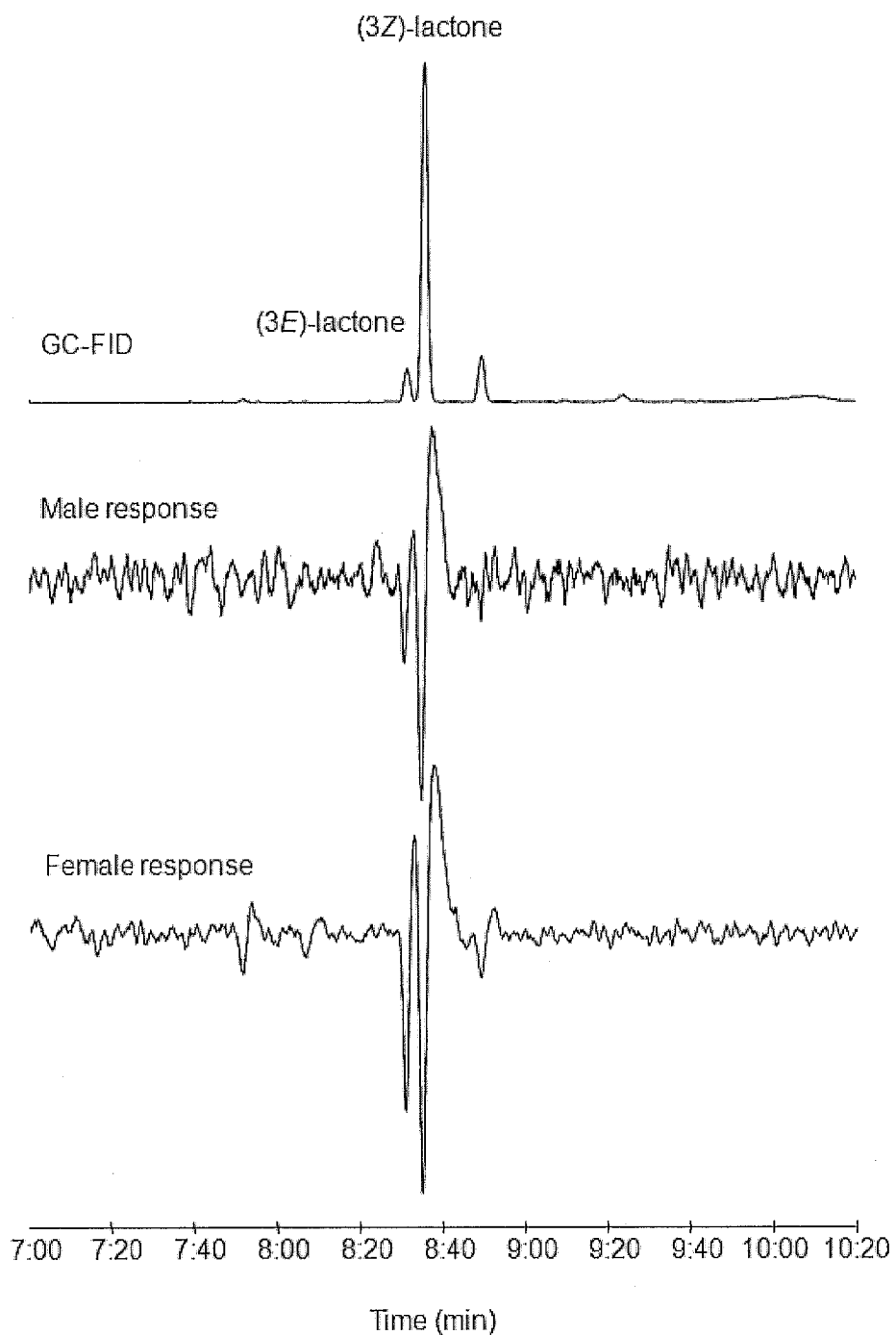

GC/EAD analysis showed responses at the retention time of (3Z)-lactone (not (3E)-lactone) produced by females only confirming previously published results (Bartelt et al. 2007). This was confirmed by GC/MS analysis. GC-FID/EAD responses of male and female *A. planipennis* antennae is shown in FIG. 4 to a synthetic mixture of (3E)- and (3Z)-lactones; note the significant responses to both stereoisomers.

Effect of Light on (3Z)-Lactone.

Exposure to UV-light had a considerable impact on the ratio of (3E):(3Z)-lactone The initial lactone sample had a (3E):(3Z) ratio of 0.028 which increased with time of exposure to UV light, reaching a ratio of 0.60 after three d. GC/MS confirmed that exposure to UV-light resulted in isomerization without producing any other secondary products except a small amount (<1%) of the conjugated isomer. Preliminary studies found that under our normal laboratory fluorescent lighting conditions, (3Z)-lactone is very stable and did not readily isomerize to the (3E)-lactone. In addition, storing (3Z)-lactone in a pyrex container filtered out the UV-light, also preventing photoisomerisation. Exposure of either lactone isomer in a quartz cuvette or on the surface of female *A. planipennis* cadavers in direct sunlight resulted in very slow isomerization even after 2-3 days.

Y-Tube Olfactometer Assays.

Figure 5:
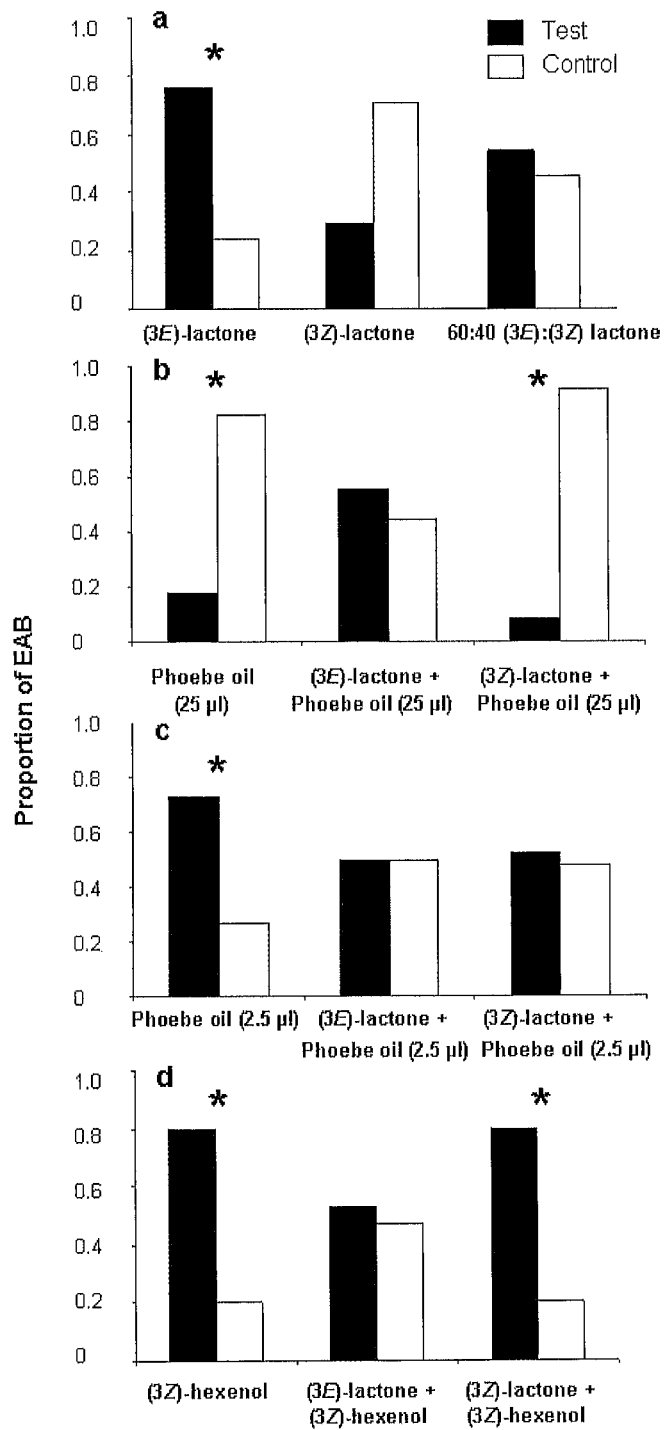

In the Y-tube olfactometer assay, males were significantly attracted to the (3E)-lactone ($\chi^2=6.76$, n=25, P=0.009), but not the (3Z)-lactone ($\chi^2=2.88$, n=17, P=0.09) or the 60:40 ratio ($\chi^2=0.17$, n=24, P=0.68) (FIG. 5a). Low doses of Phoebe oil were attractive to males ($\chi^2=5.54$, n=26, P=0.018) (FIG. 5c), whereas higher doses were significantly repellant ($\chi^2=7.12$, n=17, P=0.008) (FIG. 5b). Combining either lactone isomer with a low dose of Phoebe oil was not attractive to males ($\chi^2=0.0$, n=38, P=1.0 and $\chi^2=0.08$, n=48, P=0.773, for (3E) and (3Z)-lactone, respectively). Similarly, combining (3E)-lactone with the high dose of Phoebe oil was not attractive ($\chi^2=0.11$, n=9, P=0.74) and (3Z)-lactone combined with high dose of Phoebe oil was significantly repellant ($\chi^2=8.33$, n=12, P=0.004). Finally, males were highly attracted to (3Z)-hexenol ($\chi^2=9.0$, n=25, P=0.003) (FIG. 5d), the (3Z)-lactone+(3Z)-hexenol combination ($\chi^2=5.4$, n=15, P=0.02) (FIG. 5d), but not the (3E)-lactone+(3Z)-hexenol combination ($\chi^2=0.059$, n=17, P=0.88). Females were slightly attracted to a low dose of Phoebe oil (70% responded) ($\chi^2=3.52$, n=23, P=0.061) and to the (3Z)-hexenol (75% responded) ($\chi^2=6.00$, n=24, P=0.014), but did not respond in sufficient numbers for analysis in any other treatment.

Field Trapping.

Figure 6:
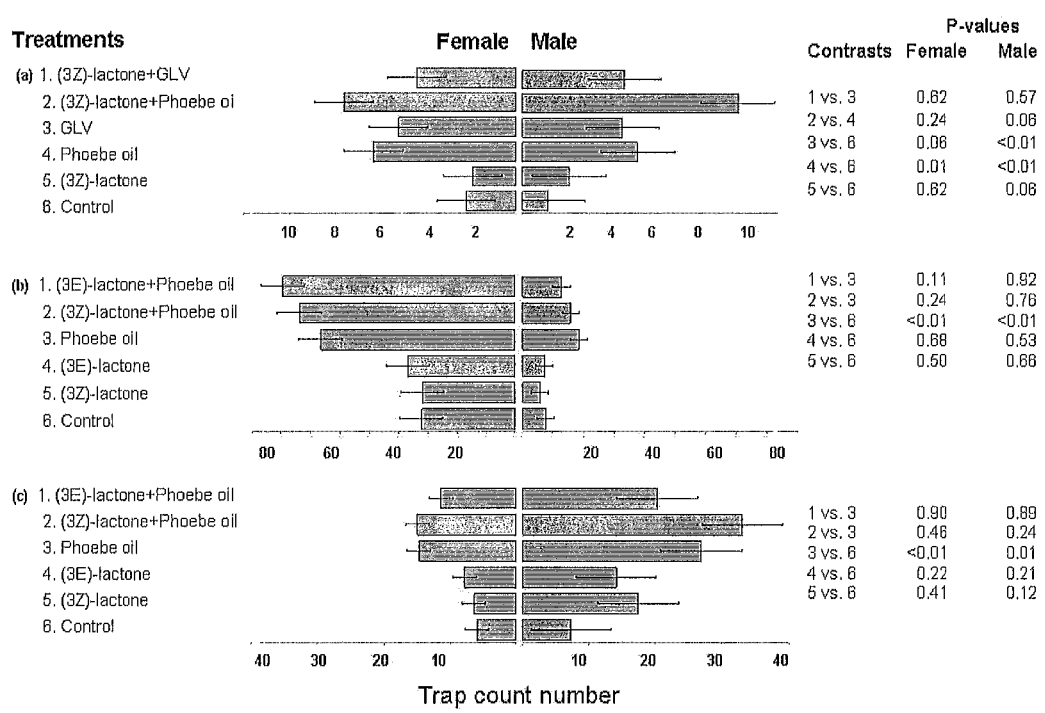

In experiment 1 (2008), both host volatile treatments increased trap captures compared to unbaited controls (FIG. 6a). Phoebe oil increased trap captures of both sexes (P<0.01) (Contrast 4 vs. 6; FIG. 6a); the GLVs increased trap capture significantly for males (P<0.01); female capture was only marginally increased (P<0.06) (Contrast 3 vs. 6; FIG. 6a). The (3Z)-lactone was not significantly attractive on its own (Contrast 5 vs. 6; P=0.06) and there was only a marginal mean catch of males when combined with Phoebe oil (P=0.06; Contrast 2 vs. 4). There was no evidence of increases in trap captures for the lactone+GLV combination on purple traps (Contrast 1 vs. 3; FIG. 6a).

In experiment 2 (2009 site 1 and site 2), Phoebe oil again increased trap captures compared to unbaited controls for both sexes at both sites (P<0.01) (Contrast 3 vs. 6; FIG. 6b, c). However, neither (3Z) nor (3E)-lactone alone, or in combination with Phoebe oil, significantly increased the number of male or female *A. planipennis* captured on purple traps (Contrast 1 or 2 vs. 3; FIG. 6b, c) as compared to the Phoebe oil alone. At one site (Union Gas), captures of females were 4× and 5× greater than captures of males for blank traps and treatments containing Phoebe oil, respectively (FIG. 6b). In contrast, trap captures were male-biased at the other site (Anika Mills).

Figure 7:
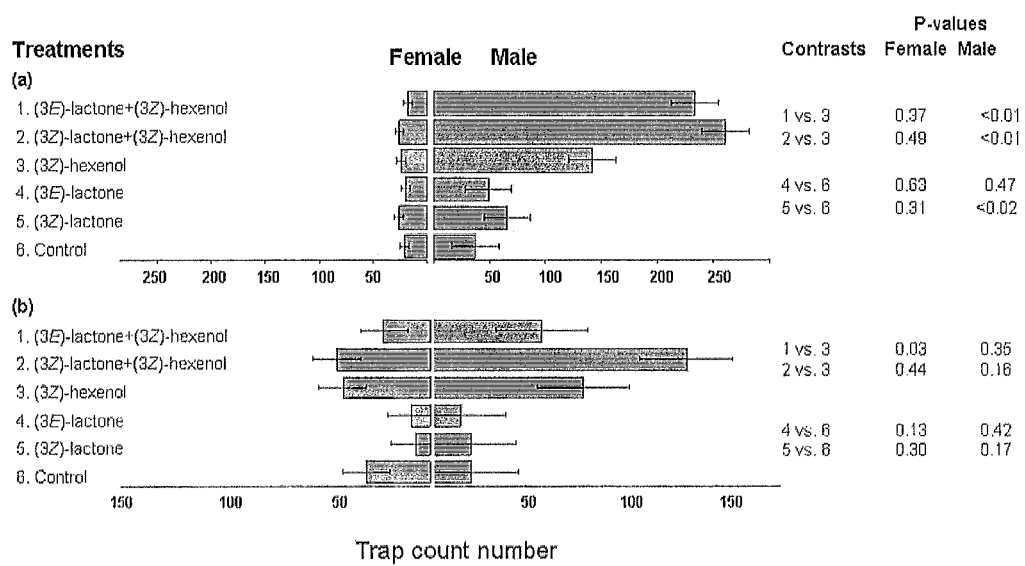

In experiment 3 (2010), as in experiment 2, the (3E)-lactone isomer by itself did not affect trap catch (Contrast 4 vs. 6; FIGS. 7a and b); however, there was a slight increase in trap captures when the (3Z)-lactone was used alone on green traps deployed in the canopy at sites in Ontario (Contrast 5 vs. 6; P<0.02) (FIG. 7a). Most importantly, there was a significant increase in captures of males at sites in Ontario when (3Z)-hexenol was combined with either (3Z)-lactone or (3E)-lactone (Contrast 1 or 2 vs. 3; P<0.01) (FIG. 7a). A similar trend was observed at sites in Michigan (FIG. 7b), although differences were not significant (P=0.16); captures of males on traps baited with (3Z)-lactone+(3Z)-hexenol was ca. 50% greater than traps baited with (3Z)-hexenol alone. Most lure treatments did not significantly affect capture of female *A. planipennis* (P>0.31) (FIGS. 7a and b), except mean female catch in traps baited with (3E)-lactone+(3Z)-hexenol was slightly lower than that in traps baited with (3Z)-hexenol alone in Michigan (P=0.03) (FIG. 7b).

Discussion

We provide the first evidence for a pheromone in a buprestid beetle that increases attraction of males to a host volatile. Our data confirms that female *A. planipennis* emit (3Z)-lactone, as observed by Bartelt et al. (2007), and demonstrates that it increases mean catch of male *A. planipennis* on green prism sticky traps when combined with the green leaf volatile, (3Z)-hexenol, and when deployed in the tree canopy. Captures of males with the (3Z)-lactone+(3Z)-hexenol was at least 50-100% greater compared to the (3Z)-hexenol alone in Michigan and Ontario, respectively. The (3E)-lactone+(3Z)-hexenol was inconsistent increasing captures of males by 60% in Ontario only. Our results are similar to the increases in trap captures observed for the combination of host kairomones and the male-produced pheromones in *Tetropium fuscum* (Fabricius) (Coleoptera: Cerambycidae) (Silk et al. 2007; Sweeney et al. 2010) and *Anaplophora glabripennis* (Motschuslky) (Nehme et al. 2010). Indeed, (3Z)-hexenol has been demonstrated to synergize pheromone attraction and function as a kairomone for a number of other beetles species (Dickens et al. 1990; Ruther et al. 2000, 2002; Ruther and Mayer 2005; Reinecke et al. 2006). (3Z)-dodecen-12-olide was previously reported as the major component of the male-produced pheromone of the flat grain beetle *Cryptolestes pusillus* (Schonherr) (Coleoptera: Cucujidae) (Millar et al. 1985).

Concerning the Ontario vs. Michigan trapping data, the inconsistent results are likely due to differences related to tree sizes and where mating activity takes place. In Michigan, trees were 10-30 m high with traps hanging at ca. 6 m. Thus, in most cases this was well below the canopy. In contrast, in Ontario the green traps were placed in mid-canopy of 4-6 m tall trees. Most of the mating activity of *A. planipennis* has been shown to occur in the canopy and in sunshine (Lance et al. 2007; Lelito et al. 2007; Rodriguez-Saona et al. 2007). Thus, trap color, lure combination, and trap deployment (i.e., trap height) may all influence attraction to the putative pheromone compounds.

Our study indicates that the type of host volatile affects attraction by *A. planipennis* to the pheromone: i.e., the lactone increased male attraction when combined with (3Z)-hexenol but not with Phoebe oil. (3Z)-hexenol elicits significant antennal responses (Rodriguez-Saona et al. 2006; de Groot et al. 2008) and consistently increased trap captures over the controls regardless of trap color (de Groot et al. 2008; Grant et al. 2010), indicating its importance as a host kairomone for *A. planipennis*. Adding other green leaf volatiles to (3Z)-hexenol tends to reduce trap captures of *A. planipennis* (Crook et al. 2008; de Groot et al. 2008; Grant et al. 2010), which could explain the lack of effect between our two-component GLV lure and the (3Z)-lactone in 2008. Our observation of increased attraction of the pheromone+green leaf volatile combination further suggests that *A. planipennis* females may call more frequently on host foliage than on host bark. Observations by others (Lance et al. 2007; Lelito et al. 2007; Rodriguez-Saona et al. 2007) that flight activity of male *A. planipennis* tends to be greatest in the upper canopy of host trees lends some support to our contention, but some mating has also been observed on the trunks of host trees (Rodriguez-Saona et al. 2007; Lelito et al. 2007).

Exposure of (3Z)-lactone to UV light in the laboratory caused a significant isomerization to the (3E)-lactone. *A. planipennis* adults tend to be most active in the upper canopy of host trees (Lelito et al. 2007) when the weather is warm and sunny (Yu 1992) so adults are naturally well exposed to sunlight. Whether or not female *A. planipennis* are exposed to sufficient UV radiation to cause partial isomerization of the (3Z)-lactone to the (3E)-lactone is unknown. However, the synthesis of insect pheromones mediated by sunlight is not unprecedented. Staples et al. (2009) recently identified a female-produced sex-pheromone of the pamphiliid sawfly, *Acantholyda erythrocephala* (L.) ((Z)-6,14-pentadecadienal) and showed that females also produce (Z,Z)-1,9,15-pentacosatriene, which is a precursor to the sex-pheromone.

Bartelt et al. (2007) noted that the (3Z)-lactone was detected with the greatest emission from females 2-4 d post emergence, which corresponds to the time when *A. planipennis* are sexually immature. These authors suggest that this may, in part, be due to declining beetle health (i.e. high mortality in the collection chamber). Our data suggest that 3 d exposure to natural sunlight on the surface of cadavers of females is not sufficient to cause photoisomerization. Our olfactometer observations indicated that the (3E)-lactone but not the (3Z)-lactone was attractive to males, and our field experiments indicate that trap captures may be significantly increased by the combination of either (3Z)- or (3E)-lactones plus (3Z)-hexenol. There is a need for further research to test whether light is an important determinant in the mating activity of *A. planipennis* and to determine what role the lactone stereoisomers play in the mating behavior.

In summary, Bartelt et al. (2007) identified a macrocyclic (3Z)-lactone that was hypothesized to act as a pheromone. Here we report the first evidence that (3Z)-lactone can significantly increase male trap catch when combined with the green leaf volatile, (3Z)-hexenol, in green traps deployed in the canopy. This provides evidence that indeed, the (3Z)-lactone is a pheromone component. It appears that two cue modalities are required by *A. planipennis* in the mate-finding process: a visual cue (green) and a two-component olfactory cue: a foliage volatile (kairomone), (3Z)-hexenol, and the pheromone, (3Z)-lactone. It is this combination we recommend to develop monitoring and early detection tools recognizing that some further improvements may come from fine-tuning each of the three components. Further research is required to optimize the kairomone component of a lure for *A. planipennis*, including release rate and ratios of chemical components. Further study is also needed to elucidate the possible biological relevance of (3Z)- and (3E)-lactone given their sex-specific effects on *A. planipennis* behavior. The mechanism of a possible photolytic interconversion of (3Z)- and (3E)-lactone is presently being studied. The effect of light on the mating behavior and pheromone production of *A. planipennis* may also be a key determinant which may translate to other *Agrilus* species.

In a further study, we use field trapping as a technique to further explore behavioral responses of *A. planipennis* to (3Z)-lactone, alone and in combination with host volatiles. Our objectives were to: 1) establish a dose-response curve of male *A. planipennis* to (3Z)-lactone in combination with (3Z)-hexenol; and 2) test the effect of trap location, specifically height with respect to the ash canopy, on attraction to (3Z)-lactone alone or in combination with (3Z)-hexenol.

Methods and Materials

Two trapping experiments were conducted in green and white ash plantations (*F. pennsylvanica* Marsch and *F. americana* L.) located 40-60 km southeast of Sarnia, Ontario in 2011. Trees were 20-30 yr old, 5-8 m tall, 12-18 cm in diameter, and spaced 2-3 m apart within and between rows. Five sites were used in total: four were green ash and the fifth was a white ash plantation. Trees at four of the sites generally appeared healthy with few or no signs of decline and only a few with obvious signs and symptoms of infestation by *A. planipennis*. At the fifth site, obvious crown decline and signs of infestation were apparent on about one-quarter of trees.

Green prism sticky traps (0.30 cm×35.00 cm×58.75 cm) (Synergy Semiochemicals Corp., Burnaby, BC) were used in all field trials, deployed using modified umbrella rig spreaders (Zing Products, Westport, Mass.). Traps were spaced 20-25 m apart and lure treatments replicated in randomized complete block designs. Traps were deployed either using ropes tied between two trees or using a single line over a canopy branch, as described further below for each specific experimental objective. Traps were typically checked every 2 wk and *A. planipennis* were collected, counted, and sexed.

Effects of Dose and Trap Height on Responses to (3Z)-Lactone

The two trapping experiments tested the (3Z)-lactone with and without (3Z)-hexenol, at different dosages and heights within the canopy. Experiment 1 was designed to determine the optimum release rate for attractiveness of (3Z)-lactone to male *A. planipennis*, in combination with (3Z)-hexenol. Dark green (540-nm wavelength) sticky traps (Francese et al 2010a) were suspended using ropes tied between two trees in the mid-canopy and baited with a (3Z)-hexenol lure at release rate of (50-100 mg/day) (Synergy Semiochemicals, Burnaby, B.C.) plus a rubber septum (Wheaton) loaded with either 0, 0.1 mg, 1.0 mg, 10.0 mg, or 50.0 mg of (3Z)-lactone. Respective release rates of the lactone were estimated as ~2.4 μg/day; ~22 μg/day; ~160 μg/day; and ~600 μg/day, based on volatile collections on Super-Q® at 25° C. (Silk et al. 2011). (3Z)-Lactone lures were estimated to last three weeks in the field and were replaced once. Trapping was conducted from 9 June-21 July. Lure treatments were replicated 10 times with eight blocks at one site (Anika Mills) and two blocks at a second site (Nauvoo Ranch). (3Z)-Hexenol lures were not changed during the experiment.

Experiment 2 was a 2×2×2 factorial experiment designed to test the effects of (3Z)-lactone, (3Z)-hexenol, trap height, and their interactions on numbers of *A. planipennis* captured on sticky, dark green (540-nm wavelength) (Francese et al 2010a) prism traps. Traps were baited with either (3Z)-lactone, (3Z)-hexenol, (3Z)-lactone+(3Z)-hexenol, or neither compound (unbaited control) and all treatments were deployed both below the canopy or in the mid-canopy. Traps placed below the canopy were suspended from ropes tied between two trees so the trap was 1-1.5 m from either tree and the top of the trap was 1.5-2 m above the ground. Traps in the canopy were deployed from a single line looped over a mid-canopy branch such that traps were 1-1.5 m from the main stem and their tops were 6 m above ground. (3Z)-Lactone was loaded onto rubber septa lures at a dosage of 3 mg/lure. Release rates of the (3Z)-lactone and (3Z)-hexenol were 60-70 μg/day and 50-100 mg/day, respectively at 25° C. Traps were in the field from 8 June-5 August, with one block at one site (Nauvoo Ranch), 5 blocks at a second site (LaSalle, the one white ash plantation), and 4 blocks at a third site (Brook Line). The 3 mg (3Z)-lactone lures were estimated to maintain adequate release rates for a minimum of three weeks and thus were replaced after three weeks; (3Z)-hexenol lures were not replaced during the experiment.

Numbers of *A. planipennis* captured in the trapping experiments were subjected to ANOVA separately for males and females. In experiment 1, ANOVA was used to test the effect of release rate on captures of females and males. Holm-Sidak comparisons were made between treatments and the control, (3Z)-hexenol alone. In experiment 2, we used the general linear model: mean catch=lactone+GLV+trap height+lactone*trap height+GLV*trap height+lactone*GLV+lactone*GLV*trap height+error, in SAS GLM (SAS Institute 1999-2003). Residuals were tested for homogeneity of variance and normality, and a ln(y+1) transformation was used where necessary. We present the untransformed last squares treatment means and their standard errors, along with statistics (P>F) from ANOVA of transformed data.

Results

Effect of Dose and Trap Height.

In experiment 1, trap capture of male *A. planipennis* on traps baited with (3Z)-lactone (in combination with (3Z)-hexenol) varied significantly with (3Z)-lactone release rate (F=2.84; df=4.45; p=0.035). Captures of males were highest at the lowest dose of 0.1 mg (equivalent to release rate of 2.4 μg/day at 25° C.) of (3Z)-lactone, as compared to (3Z)-hexenol alone (p=0.003) (FIG. 1). There was also a marginal increase in captures of males at the 1.0 mg dose of (3Z)-lactone, as compared to the control (p=0.052). Trap capture of female *A. planipennis* was not influenced by (3Z)-lactone release rate (F=1.22; df=4.45; p=0.315) (FIG. 8).

In experiment 2, mean capture of males per trap was significantly and positively affected by presence of the lactone (F=7.46; df=1.63; P=0.008), the (3Z)-hexenol (F=36.2; df=1.63; P<0.0001), and by trap height (F=61.4; df=1.63; P<0.0001); none of the interactions were significant (F<1.15; df=1.63; P>0.25). Mean catch of females was significantly affected by trap height (F=32.7; df=1.63; P<0.001) but not by the lactone (F=0.18; df=1.63; P=0.67), (3Z)-hexenol (F=1.24; df=1.63; P=0.27), or any interaction (F<0.52; df=1.63; P>0.45). Mean (±SE) catch per trap of males and females respectively was 86.8 (13.7) and 15.3 (2.3) in high traps compared to 17.6 (2.3) and 5.2 (0.81) in low traps. The highest mean catch of both males and females was in traps baited with both the lactone and (3Z)-hexenol placed high in the canopy (FIG. 9b).

Discussion

We provide the first demonstration of the importance of pheromone release rate for the trap capture of male *A. planipennis*. Males were significantly attracted to low release rates of (3Z)-lactone, with a subsequent decline in captures of males with release rates exceeding ca. 160 μg/day. Significant increases in captures of males occurred in our previous study where the pheromone release rate was ca. 22 μg/day. Too-high release rates may confuse or repel males, as demonstrated in previous studies on optimum pheromone emission rates for other species (Vacas et al. 2009). Bartelt et al. (2007) reported an emission rate of approx. 10.7 ng/d of (3Z)-lactone per female *A. planipennis*. Based on Bartelt et al.'s (2007) emission estimate, the 0.1 mg lure would thus represent approx. 200 female equivalents. This may explain the apparent lack of response of males to higher levels of (3Z)-lactone in previous field trials described above: no significant attraction by males occurred in field trials where the release rate was much higher (80 μg/day and ca. 0.5 mg/day in 2008 and 2009, respectively), although different host volatiles were also being tested. In addition, the lack of attraction to (3Z)-lactone in the olfactometer bioassay study described above might be related to the dose used in that bioassay. (3Z)-Lactone released at an even lower doses than those tested in our current study may increase male attraction even further.

To optimize (3Z)-lactone release rate, its timing and level of production by females requires further investigation.

Our results confirm earlier reports that traps placed high in the canopy of ash trees catch more *A. planipennis* than low traps, and that (3Z)-hexenol significantly increase trap catch of *A. planipennis*. All three factors influenced catch of males in an additive, positive fashion. Thus, of all the trap-lure combinations we tested, green traps baited with (3Z)-hexenol and (3Z)-lactone, placed high in the canopy of ash trees, are likely to have the greatest probability of detecting male *A. planipennis* where it is present. This is perhaps not surprising because most of the flight and mating activity of *A. planipennis* has been shown to occur in the canopy of ash trees and in sunshine (Lance et al. 2007, Lelito et al. 2008, Rodriguez-Saona et al. 2007). The strong effect of trap height on catch of both sexes of *A. planipennis* may explain some inconsistencies in previous studies which found the (3Z)-lactone+(3Z)-hexenol combination was only significantly attractive at sites where traps were placed well within the ash canopy.

In summary, Bartelt et al (2007) identified a macrocyclic lactone, (3Z)-dodecen-12-olide that was hypothesized to act as a pheromone. We reported here the first evidence that (3Z)-lactone can significantly increase the number of males captured, especially when combined with the green leaf volatile, (3Z)-hexenol, on green traps deployed in the canopy. In this study we have conclusively demonstrated that (3Z)-lactone alone is attractive to male *A. planipennis*, that male attraction decreases when the lactone release rate is too high, and that the combination of (3Z)-lactone, (3Z)-hexenol, and placement of traps high in the canopy of ash trees results in greatest mean catch of male *A. planipennis*. It appears that two cue modalities are used by male *A. planipennis* in the mate-finding process: a visual cue (green) and a two-component olfactory cue: a foliage volatile (kairomone), (3Z)-hexenol, and the sex pheromone, (3Z)-lactone. This study furthers our understanding of the behaviour of *A. planipennis* in response to its volatile pheromone and host volatiles, and contributes both to knowledge of its chemical ecology and the development of improved tools for its early detection. We suggest that use of green traps placed high in the canopy and baited with (3Z)-hexenol and (3Z)-lactone will increase the efficacy of detecting low density populations of *A. planipennis* in trapping surveys. Additional research is required to optimize the release rate of (3Z)-lactone as well as the release rate and ratio of kairomone component of the lure for *A. planipennis*.

REFERENCES CITED

Analytical Software. 1998. Statistix for Windows User's Manual. Analytical Software, Tallahassee, Fla.

Article I. Akers, R. C., and D. G. Nielsen. 1992. Mating behavior of the bronze birch borer (Coleoptera: Buprestidae). J. Entomol. Sci. 27: 44-49.

Bartelt, R, A. A. Cosse, B. W. Zilkowski, and I. Fraser. 2007. Antennally active macrolide from the emerald ash borer *Agrilus planipennis* emitted predominantly by females. J. Chem. Ecol. 33:1299-1302.

Blakemore, P. R., W. J. Cole, P. J. Kocieński, and A. Morley. 1998. A stereoselective synthesis of trans-1,2-disubstituted alkenes based on the condensation of aldehydes with metallated 1-phenyl-1H-tetrazol-5-yl sulfones. Synlett. 26-28.

Boden, C. D. J., J. Chambers, and D. R. Stevens. 1993. A concise, efficient and flexible strategy for the synthesis of the pheromones of *Oryzaephilus* and *Cryptolestes* grain beetles. Synthesis. 4: 411-420.

Cappaert, D., D. G. McCullough, T. M. Poland, and N. W. Siegert. 2005. Emerald ash borer in North America: a research and regulatory challenge. Am. Entomol. 51:152-165.

Carlson, R. W., and F. B. Knight. 1969. Biology, taxonomy, and evolution of sympatric *Agrilus* beetles (Coleoptera: Buprestidae). Contr. Am. Entomol. Inst. 3: 1-105.

Cossé, A. A., and R. J. Bartelt. 2000. Male-produced aggregation pheromone of *Colopterus truncatus*: structure, electrophysiological and behavioral activity. J. Chem. Ecol. 26:1735-1748.

Crook, D. J., A. Krimian, J. Francese, I. Fraser, T. M. Poland, A. J. Sawyer, and V. C. Mastro. 2008. Development of a host-based semiochemical lure for trapping emerald ash borer *Agrilus planipennis* (Coleoptera: Buprestidae). Environ. Entomol. 37: 356-365.

Crook, D. J., J. A. Francese, K. E. Zylstra, I. Fraser, A. J. Sawyer, D. W. Bartells, D. R. Lance, and V. C. Mastro. 2009. Laboratory and field response of emerald ash borer (Coleoptera: Buprestidae), to selected regions of the electromagnetic spectrum. J. Econ. Entomol. 102: 2160-2169.

Crook, D. J., and V. C. Mastro. 2010. Chemical ecology of the emerald ash borer. J. Chem. Ecol. 36: 101-112.

de Groot, P., W. D. Biggs, D. B. Lyons, T. Scarr, E. Czwerwinski, H. J. Evans, W. Ingram, and K. Marchant. 2006. A visual guide to detecting emerald ash borer damage. Natural Resources Canada and Ontario Ministry of Natural Resources, Sault Ste. Marie, Ontario, Canada.

de Groot, P., G. G. Grant, T. M. Poland, R. Scharbach, L. Buchan, R. W. Nott, L. MacDonald, and D. Pitt. 2008. Electrophysiological response and attraction of emerald ash borer to green leaf volatiles (GLVs) emitted by host foliage. J. Chem. Ecol. 34: 1170-1179.

Dickens, J. C., E. B Jang, D. M. Light, and A. R. Alford. 1990. Enhancement of insect pheromone responses by green leaf volatiles. Naturwissenschaften 77: 29-31.

Dunn, J. P., and D. A. Potter. 1988. Evidence for sexual attraction by the two-lined chestnut borer, *Agrilus bilineatus* (Weber) (Coleoptera: Buprestidae). Can. Entomol. 120:1037-1039

EAB. 2010. Emerald ash borer information. www.emeraldashborer.info.

Ephrussi, B., and G. W. Beadle. 1936. A technique of transplantation for *Drosophila*. Am. Nat. 70:218-225.

Francese, J. A., V. C. Mastro, J. B. Oliver, D. R. Lance, N. Youssef, and S. G. Lavalee. 2005. Evaluation of colors for trapping *Agrilus planipennis* (Coleoptera: Buprestidae). J. Entomol. Sci. 40: 93-95.

Francese, J. A., I. Fraser, D. R. Lance, and V. C. Mastro. 2007. Developing survey techniques for emerald ash borer: the role of trap height and design, pp. 72-73. In Proceedings: Emerald ash borer research and technology development meeting, US Department of Agriculture Forest Health Technology Enterprise Team FHTET-2005-16, 26-27 Sep. 2005, Pittsburgh, Pa., USA.

Francese, J. A., D. J. Crook, I. Fraser, D. R. Lance, A. J. Sawyer, and V. C. Mastro. 2008. Further investigations in developing a trap for emerald ash borer: how trap height affects capture rates. In: Emerald Ash Borer Research and Development Meeting FHTET 2007-08. Comp. by Mastro, V, Lance D, Reardon R, Parra G, USDA, Forest Service, Morgantown, W. Va., p. 79-80.

Francese, J. A., D. J. Crook, I. Fraser, D. R. Lance, A. J. Sawyer, and V. C. Mastro. 2010a. Optimization of trap color for the emerald ash borer, *Agrilus planipennis* (Coleoptera: Buprestidae). J. Econ. Entomol. 103: 1235-1241.

Francese et al. 2010b. Relation of prism trap color, size and canopy placement in determining capture of emerald ash borer(Coleoptera: Buprestidae) Can. Entomol. 142: 596-600.

Grant, G. G., K. L. Ryall, D. B. Lyons, and M. M. Abou-Zaid. 2010. Differential response of male and female emerald ash borers (Col., Buprestidae) to (Z)-3-hexenol and Manuka oil. J. Appl. Entomol. 134: 26-33.

Gwynne, D. T., and D. C. F. Rentz. 1983. Beetles on the bottle: male buprestids mistake stubbies for females (Coleoptera). J. Austral. Entomol. Soc. 23: 79-80.

Heath, R. R., and P. E. Sonnet. 1980. Technique for in situ coating of $Ag^+$ onto silica gel in HPLC columns for the separation of geometrical isomers. J. Liq. Chromatogr. 3:1129-1135.

Justus, K., and W. Steglich. 1991. First synthesis of a strained 14-membered biaryl lactone ether by macrolactonization. Tetrahedron Letters. 32: 5781-5784.

Kurihara, T., Y. Nakajima, and O. Mitsunobu. 1976. Synthesis of Lactones and cycloalkanes. Cyclization of w-hydroxy acids and ethyl α-cyano-w-hydroxycarboxylates. Tetrahedron Letters. 28: 2455-2458.

Lance, D. R, I. Fraser, and V. C. Mastro. 2007. Activity and microhabitat-selection patterns for emerald ash borer and their implications for the development of trapping systems. In: Emerald Ash Borer Research and Asian Longhorned Beetle Research and Technology Development Meeting, FHTET 2007-04. Comp. by Mastro V, Lance D, Reardon R, Parra G, USDA, Forest Service, Morgantown, W. Va., p. 77-78.

Lelito, J. P., I. Fraser, V. C. Mastro, J. H. Tumlinson, K. Boroczky, and T. C. Baker. 2007. Visually mediated 'paratrooper copulations' in the mating behaviour of *Agrilus planipennis* (Coleoptera: Buprestidae), a highly destructive invasive pest of North American ash trees. J. Insect. Behay. 20:537-552.

Lelito, J. P., I. Fraser, V. C. Mastro, J. H. Tumlinson, and T. C. Baker. 2008. Novel visual-cue-based sticky traps for monitoring of emerald ash borers, *Agrilus planipennis* (Col., Buprestidae). J. Appl. Entomol. 132: 668-674.

Lelito, J. P., K. Böröczky, T. H. Jones, I. Frazer, V. C. Mastro, J. H. Tumlinson, and T. C. Baker. 2009. Behavioral Evidence for a Contact Pheromone Component of the Emerald Ash Borer, *Agrilus planipennis* Fairmaire. J. Chem. Ecol., 35:104-110.

Lindgren, B. O., and T. Nilsson. 1973. Preparation of carboxylic acids from aldehydes (including hydroylated benzaldehydes) by oxidation with chlorite. Acta Chemica *Scandinavica.* 27: 888-890.

Lyons, D. B., P. de Groot, G. C. Jones, and R. Scharbach. 2009. Host selection by *Agrilus planipennis* (Coleoptera: Buprestidae): inferences from sticky-band trapping. Can. Entomol. 141: 40-52

Marchant, K. R. 2006. Managing the emerald ash borer in Canada-2005, p.2. In Proceedings: Emerald ash borer research and technology development meeting, US Department of Agriculture Forest Health Technology Enterprise Team FHTET-2005-16, 26-27 Sep. 2005, Pittsburgh, Pa., USA.

McCullough, D. G., T. M. Poland, and D. L. Cappaert. 2006. Attraction of emerald ash borer to trap trees: Effects of stress agents and trap height, pp. 61-62. In Proceedings: Emerald ash borer research and technology development meeting, US Department of Agriculture Forest Health Technology Enterprise Team 26-27 Sep. 2005, Pittsburgh, Pa., USA.

McCullough, D. G., T. M. Poland, A. C. Anulewicz, and D. L. Cappaert. 2008. Double-deckers and towers: Emerald ash borer traps in 2007, pp. 73-75. In V. Mastro, D. Lance, R. Reardon and G. Parra (eds.). Proceedings of the emerald ash borer and asian longhorned beetle research and technology development meeting, Pittsburgh, Pa., 23-24 Oct. 2007. FTTET-2008-07, USDA Forest Service Forest Health Technology Enterprise Team, Morgantown, W. Va.

McCullough, D. G., T. M. Poland, and D. L. Cappaert. 2009. Emerald ash borer (Coleoptera: Buprestidae) attraction to stressed or baited ash trees. Environ. Entomol. 38: 1668-1679.

Millar, J. G., H. D. Pierce, JR., A. M. Pierce, A. C. Oehlschlager, J. H. Borden, and A. V. Barak. 1985. Aggregation pheromones of the flat grain beetle *Crytoplestes pusillus* (Coleoptera: Cucujidae). J. Chem. Ecol. 11:1053-1070.

Nehme, M. E., M. A. Keena, A. Zhang, T. C. Baker, Z. Zhu, and K. Hoover. 2010. Evaluating the use of Male-Produced Pheromone Components and Plant Volatiles in Two Trap Designs to Monitor *Anoplophora glabripennis*. Environ. Entomol. 39:169-176.

Poland, T. M., and D. G. McCullough. 2006. Emerald ash borer: Invasion of the urban forest and the threat to North America's ash resource. J. For. 104:118-124.

Poland T. M., P. de Groot, G. Grant, L. Macdonald, and D. G. McCullough. 2004. Developing attractants and trapping techniques for the emerald ash borer. In: Emerald Ash Borer Research and Technology Development Meeting, FHTET-2004-02. Comp. by Mastro V and Reardon R, USDA Forest Service, Morgantown, W. Va. p. 15-16.

Poland, T. M., D. G. McCullough, P. de Groot, G. G. Grant, L. MacDonald, and D. L. Cappaert. 2005. Progress toward developing trapping techniques for the emerald ash borer, pp. 53-54. In Proceedings: Emerald Ash Borer Research and Technology Development Meeting, US Department of Agriculture Forest Health Technology Enterprise Team, Morgantown, W. Va., USA.

Poland T. M., C. Rodriguez-Saona, G. G. Grant, L. Buchan, P. de Groot, J. Miller, and D. G. McCullough. 2006. Trapping and detection of emerald ash borer: Identification of stress-induced volatiles and tests of attraction in the lab and field. In: Emerald Ash Borer Research Technology Development Meeting, FHTET-2005-16. Comp. by Mastro V, Reardon R, Parra G, USDA Forest Service, Morgantown W. Va., p. 64-65.

Poland, T. M., D. S. Pureswaren, G. G. Grant, and P. de Groot. 2007. Field attraction of emerald ash borer to antenally and behaviorally active ash volatiles, pp. 80-81. In Proceedings: Emerald Ash Borer Research and Technology Development Meeting, US Department of Agriculture Forest Health Technology Enterprise Team 20 Oct.-2 Nov., 2006, Cincinnati, Ohio, USA.

Pureswaran, D. S., and T. M. Poland. 2009 The role of olfactory cues in short-range mate finding by the emerald ash borer, *Agrilus planipennis*, Fairmaire (Coleoptera: Cerambycidae). J. Insect. Behav. 22: 205-216.

Reinecke A., J. Ruther, C. J. Mayer, and M. Hilker. 2006. Optimized trap lure for male *Melolontha* cockchafers. J. Appl. Entomol. 130, 171-176.

Rodriguez-Saona, C., T. M. Poland, J. R. Miller, L. L. Stelinski, G. G. Grant, P. de Groot, L. Buchan, and L. MacDonald. 2006. Behavioral and electrophysiological responses of the emerald ash borer, *Agrilus planipennis*, to induced volatiles of Manchurian Ash, *Fraxinus mandshurica*. Chemoecology 16:75-86.

Rodriguez-Saona, C. R., J. R. Miller, T. M. Poland, T. M. Kuhn, G. W. Otis, T. Turk, and D. L. Ward. 2007. Behaviors of adult *Agrilus planipennis* (Coleoptera: Buprestidae). Great Lakes Entomol. 40:1-16.

Ruther J., A. Reinecke, K. Thiemann, T. Tolasch, W. Francke, and M. Hilker. 2000. Mate finding in the forest cockchafer, *Melolontha hippocastani*, mediated by volatiles from plants and females. Physiol. Entomol. 25: 172-179.

Ruther J., A. Reinecke, and M. Hilker. 2002. Plant volatiles in the sexual communication of *Melolontha hippocastani*: response toward time dependent bouquets and novel function of (Z)-3-hexen-1-ol as a sexual kairomone. Ecol. Entomol. 27, 76-83.

Ruther J., and C. J. Mayer. 2005. Response of garden chafer, *Phylloertha horticola*, to plant volatiles: from screening to application. Entomol. Exp. Appl. 115: 51-59.

Schlosser M., and K. F. Christmann. 1966. Trans-Selective Olefin Syntheses. Angew. Chem. Internet. Edit. 5:126.

Seigert, N. W., D. G. McCullough, A. M. Liebhold, and F. W. Telewski. 2007. Resurrected from the ashes: A historical reconstruction of emerald ash borer dynamics through dendrochronological analysis. In: Emerald ash borer and Asian longhorned beetle research and technology development meeting. FHTET-2007-04. Comp. by Mastro V, Lance D, Reardon R, Parra G, Forest Health Technology Enterprise Team, Morgantown, W. Va., 18-19.

Silk, P. J., K. Ryall, B. Lyons, J. D. Sweeney, and J. Wu. 2009. A Contact Sex Pheromone Component of the Emerald Ash Borer *Agrilus planipennis* Fairmaire (Coleoptera: Buprestidae). Naturwissenchaften. 96: 601-608.

Silk, P. J., K. Ryall, P. Mayo P, M. Lemay, G. Grant, D. Crook, A. Cosse, I. Fraser, J. D. Sweeney, D. B. Lyons, D. Pitt, T. Scarr, and D. Magee. 2011. Evidence for a volatile pheromone in *Agrilus planipennis* Fairmaire (Coleoptera: Buprestidae) that increases attraction to a host foliar volatile. Environ. Entomol. 40: 904-916.

Silk, P. J., J. D. Sweeney, J. Wu, J. Price, J. Gutowski, and E. G. Kettela. 2007. Evidence for a male-produced pheromone in *Tetropium fuscum* (F.) and *Tetropium cinnamopterum* (Kirby) (Coleoptera: Cerambycidae). Naturwissenschaften. 94:697-701.

Staples J. K., R. J. Bartelt, A. A. Cossé, and D. W. Whitman. 2009. Sex Pheromone of the Pine False Webworm *Acantholyda erythrocephala*. J. Chem. Ecol. 35:1448-1460.

Sweeney, J. D, P. J. Silk, J. M. Gutowski, J. Wu, M. Lemay, P. D. Mayo, and D. Magee. 2010. Effect of Chirality, Release Rate and Host Volatiles on Response of *Tetropium fuscum* (F.), *Tetropium cinnamopterum* (L.) Kirby and *Tetropium castaneum* (L.) to the Aggregation Pheromone, Fuscumol. J. Chem. Ecol., 36:1309-1321.

Yu, C. M. 1992. *Agrilus marcopoli* Obenberger (Coleoptera: Buprestidae), pp. 400-401.In: G. Ziao (ed.), Forest insects of China, $2^{nd}$ edition. China Forestry Publishing House, Beijing, China.

Vacas, S., C. Alfaro, V. Navarro-Llopis, M. Zarzo, and J. Primo. 2009. Study on optimum pheromone release rate for attraction of *Chilo suppressalis* (Lepidoptera: Pyralidae). J. Econ. Entomol. 102: 1094-1100.

The invention claimed is:

1. A method for the attraction of sexually mature male *A. planipennis*, comprising applying to an insect habitat a colored trap comprising an insect attracting effective amount of (3Z)-dodecen-12-olide and 3(Z)-hexenol, wherein the trap has a color in the green range of the visible light spectrum and wherein the amount of (3Z)-dodecen-12-olide is a source dosage which emits 2.4-160 µg of (3Z)-dodecen-12-olide per day, and wherein the amount of (3Z)-hexenol is a source dosage which emits 50-100 mg of (3Z)-hexenol per day, at about 25° C.

2. A method according to claim 1, wherein the insect habitat is a tree canopy.

3. A method according to claim 2, wherein the tree canopy is the upper tree canopy.

4. A method according to claim 1, wherein the trap is a prism sticky trap of a green color defined by a wavelength of 540-560 nm and a reflectance of 24-64%.

5. A method according to claim 4, wherein the trap is of a green color defined by a wavelength of about 540 nm and a reflectance of 49%, and includes an insecticide.

6. A method according to claim 1, wherein the amount of (3Z)-dodecen-12-olide emitted is 2.4-22 µg per day and the amount of (3Z)-hexenol emitted is 40-60 mg per day.

7. A method according to claim 6, wherein the amount of (3Z)-dodecen-12-olide emitted is 2.4 µg/day at 25° C.

\* \* \* \* \*